United States Patent
Lee et al.

(10) Patent No.: US 10,745,737 B2
(45) Date of Patent: Aug. 18, 2020

(54) METHODS AND REAGENTS FOR GLYCOPROTEOMICS

(71) Applicant: Children's Medical Center Corporation, Boston, MA (US)

(72) Inventors: Richard S. Lee, Weston, MA (US); Hui Zhou, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 63 days.

(21) Appl. No.: 14/441,562

(22) PCT Filed: Nov. 7, 2013

(86) PCT No.: PCT/US2013/069017
§ 371 (c)(1),
(2) Date: May 8, 2015

(87) PCT Pub. No.: WO2014/074756
PCT Pub. Date: May 15, 2014

(65) Prior Publication Data
US 2015/0291996 A1    Oct. 15, 2015

Related U.S. Application Data

(60) Provisional application No. 61/724,850, filed on Nov. 9, 2012.

(51) Int. Cl.
*C12Q 1/34*        (2006.01)
*G01N 33/68*    (2006.01)

(52) U.S. Cl.
CPC .............. *C12Q 1/34* (2013.01); *G01N 33/68* (2013.01); *G01N 2333/4728* (2013.01); *G01N 2333/98* (2013.01); *G01N 2440/38* (2013.01); *G01N 2570/00* (2013.01)

(58) Field of Classification Search
None
See application file for complete search history.

(56) References Cited

U.S. PATENT DOCUMENTS 8,785,139 B2 *   7/2014   Weber ............... G01N 33/6842
                                                        424/130.1

FOREIGN PATENT DOCUMENTS

| WO | WO 90/04596 A1 | 5/1990 |
|---|---|---|
| WO | WO1990/004596 | * 5/1990 |
| WO | WO2013/192530 | * 12/2013 |

OTHER PUBLICATIONS

Zhou et al. PNGase F catalyzes de-N-glycosylation in a domestic microwave. Anal Biochem. Aug. 1, 2012;427(1):33-5. doi: 10.1016/j.ab.2012.04.011. Epub Apr. 16, 2012.*
Butler et al., Reversible blocking of peptide amino groups by maleic anhydride. Biochem J. Jun. 1967;103(3):78P-79P.
Doerr, Glycoproteomics. Nat Meth Dec. 28, 2012;9(1):36.
Kaliberda, [Enzymes for studying the carbohydrate structure of glycoproteins]. Bioorg Khim. May 1991;17(5):581-95. Review. Russian.
Palacián et al., Dicarboxylic acid anhydrides as dissociating agents of protein-containing structures. Mol Cell Biochem. Sep. 21, 1990;97(2):101-11.
Rusmini et al., Protein immobilization strategies for protein biochips. Biomacromolecules. Jun. 2007;8(6):1775-89.
Vinogradov et al., [Deglycosylation of glycoproteins]. Bioorg Khim. Nov. 1998;24(11):803-15. Review. Russian.
Walsh et al., Post-translational modifications in the context of therapeutic proteins. Nat Biotechnol. Oct. 2006;24(10):1241-52.
Yang et al., Solid-phase glycan isolation for glycomics analysis. Proteomics Clin Appl. Dec. 2012;6(11-12):596-608. doi: 10.1002/prca.201200045.

* cited by examiner

*Primary Examiner* — Maury A Audet
(74) *Attorney, Agent, or Firm* — Wolf, Greenfield & Sacks, P.C.

(57) ABSTRACT

Methods, reagents, and kits for the reversible immobilization of glycoproteins to a solid support, the release and capture of a glycan portion of the glycoprotein, and the subsequent release and capture of the polypeptide portion of the glycoprotein are provided. The disclosure also provides suitable solid support materials, surface chemistries, and devices for use in the disclosed methods. The methods, reagents, kits, and devices provided herein are useful for the analysis of protein glycosylation, for example, in a diagnostic context, in the context of proteoglycomics, and in the context of producing glycosylated proteins for therapeutic purposes.

15 Claims, 7 Drawing Sheets

METHODS AND REAGENTS FOR GLYCOPROTEOMICS

RELATED APPLICATION

This application is a national stage filing under 35 U.S.C 371 of International Application PCT/US2013/069017, filed Nov. 7, 2013, which claims the benefit under 35 U.S.C. § 119(e) of U.S. provisional application Ser. No. 61/724,850, filed Nov. 9, 2012, and entitled Methods and Reagents for Glycoproteomics the content of both of which are incorporated by reference herein in their entirety. International Application PCT/US2013/069017 was published under PCT Article 21(2) in English.

FUNDING

This invention was made with government support under grant(s) DK077836/DK077836-03S1 awarded by the National Institutes of Health (NIH) and the National Institute of Diabetes and Digestive and Kidney Diseases (NIDDK). This government has certain rights in the invention.

BACKGROUND

The most abundant post-translational modification of proteins, glycosylation, remains practically unexplored to date at the proteome scale because of a dearth of methods for profiling the complex glycoproteome. Glycosylation of proteins plays an important role in many biological processes, including, for example, cell signaling, cell-cell interactions and the immune response. Further, the majority of protein-based biopharmaceuticals approved or in clinical trials bear some form of post-translational modification (PTM), which, in some cases, can profoundly affect protein properties relevant to their therapeutic application. A better understanding of the biological functions of glycosylation will facilitate the engineering of next-generation protein and peptide therapeutics with glycosylation profiles optimized for the respective therapeutic approach.

Analyzing the glycoproteome is technically challenging, because, as a post-translational process, glycosylation is non-templated, and, unlike other post-translational modifications (e.g., phosphorylation or methylation), glycan structures found on glycosylated proteins are highly complex. A single protein can have tens or hundreds of different glycan attachments, and glycosylated forms of proteins are often found in low abundance in the cell. The very different chemistries of proteins and glycans present additional challenges in applying analytic methods, such as mass spectrometry, in the glycoproteomic context, and current methods for isolating and/or separating glycoproteins for analytical processing lack in performance. See Doerr, Glycoproteomics Nat Meth 2012, 9(1):36, and Walsh et al., Post-translational modifications in the context of therapeutic proteins Nat Biotech 2006 24(10).

SUMMARY

Protein glycosylation is one of the most frequent post-translational modifications and is involved in many biological processes such as, for example, quality control of nascent glycoproteins, protein folding and stability, cell-cell signal transduction, and cellular adhesion. Alterations of N-glycosylation have been reported to be associated with the progress of various kinds of cancers. Moreover, glycosylation fidelity is essential for efficacy and safety of therapeutic glycoproteins. Characterization of glycans comprised in glycoproteins typically requires the release and separation of the glycan portion from the protein portion. Different approaches for glycan release are described herein that allow for rapid, reproducible, high-throughput, and unbiased glycan and protein separation, and preservation. The released glycans and proteins are suitable for downstream processing and analysis, e.g., for characterization of glycan structure or for sequence analysis of the protein. Some of the approaches described herein allow for the identification of glycosylation sites in glycoproteins as well as for an analysis of glycan occupancy at glycosylation sites.

Some aspects of this disclosure are based on the recognition that there is a need for methods that allow one or more of the following: 1) release a glycan from a protein, 2) separate glycan and protein in a manner that maintains the integrity of both glycan and protein for downstream analysis (including, but not limited to, identification of glycosylation sites and analysis of glycosylation site occupancy, as well as identification of glycan and polypeptide structure/sequence), and 3) accomplish glycan release and/or separation from a glycoprotein in a rapid, scalable manner, without cumbersome preparation or cleanup.

Some aspects of this disclosure are based on the recognition that efficient methods for isolating and analyzing glycan chains from glycosylated proteins are desirable and are a prerequisite for the analysis of protein glycosylation on proteomic scale. Most conventional methods currently in use do not allow for the recovery of the glycan and the polypeptide portions from glycosylated proteins, but only for one of the two portions. Further, most methods currently in use for separating or isolating a glycan and/or a protein portion from glycoproteins are also time consuming, labor intensive and costly, which is prohibitive to their broad use in research and diagnostics.

Some aspects of this disclosure provide a technology that is useful for releasing and separating carbohydrates, e.g., glycans, from glycoproteins and that allows for the subsequence recovery of both the glycan and the polypeptide portion of the glycoprotein. The technology described herein can be used, for example, in glycosylation analysis of glycoproteins, and can be scaled to be used for the analysis of a single glycoprotein, or for glycoproteome-wide analyses. Glycosylation analysis according to aspects of the technology provided herein, is useful for diagnostic purposes, for example, to detect aberrant glycosylation or glycosylation associated with a disease or disorder in a patient, and for quality control procedures, e.g., in the context of engineered proteins, such as therapeutic antibodies and antibody fragments. In some embodiments, glycosylation analysis according to aspects of this invention can be used for quality control of therapeutic glycoproteins (e.g., glycan occupancy of glycosylation sites for therapeutic antibodies or proteins).

The technology described herein overcomes some of the drawbacks of current methodologies and allows to separate and/or isolate both the glycan portion and the polypeptide portion of a glycoprotein while maintaining the structural integrity of each component for downstream analysis, opening up new avenues for glycoproteomic analysis in both clinical and research contexts. Separation of the glycan and polypeptide portions comprised in a glycoprotein can be performed in a selective way by using the methods provided herein, which is useful, e.g., if a specific, known polypeptide or carbohydrate or glycan is to be investigated. Alternatively, such separation of glycan and polypeptide portions of glycoproteins can be performed in an unbiased manner, which is particularly useful for glycoproteomics applications.

Some aspects of this disclosure relate to the recognition that separation of glycan and polypeptide portions of a glycoprotein can be facilitated by immobilizing the glycoprotein on a solid support, e.g., a resin, membrane, or bead. Such immobilization can be achieved by conjugating the glycoprotein to the solid support, e.g., via covalently binding the glycoprotein using an appropriate surface chemistry. Once the glycoprotein is immobilized, the glycan portion of the glycoprotein can be released, e.g., by enzymatic digest, and the intact, released glycan portion can be recovered, e.g., by elution from the solid support. Some aspects of this disclosure relate to the recognition that the protein portion of the glycoprotein can subsequently be recovered by releasing the conjugated protein from the solid support. This can be achieved by reversing the conjugation reaction, e.g., via reversing a chemical reaction that formed a covalent bond between the glycoprotein and the solid support.

Some aspects of this disclosure provide methods for separating and/or isolating a glycan from a glycoprotein comprising the glycan bound to a polypeptide. In some embodiments, the method comprises contacting the glycoprotein with a solid support that binds the polypeptide, cleaving a bond between the glycan and the polypeptide, and separating the glycan from the polypeptide. In some embodiments, the method further comprises isolating the glycan and/or the polypeptide. In some embodiments, the binding of the solid support to the polypeptide is unspecific and/or unbiased binding. In some embodiments, the solid support comprises a binding moiety that binds the polypeptide via a covalent bond, a hydrogen bond, an ionic bond, van der Waals forces, hydrophobic interactions, or π-π stacking. In some embodiments, the binding moiety is a reactive moiety that reacts with the polypeptide, forming a covalent bond between the solid support and the polypeptide. In some embodiments, the reactive moiety reacts with the amino group of the N-terminus of the polypeptide, with the carboxy group of the C-terminus of the polypeptide, or with an amino acid side chain of the polypeptide. In some embodiments, the reactive moiety comprises an acid anhydride (AA) moiety. In some embodiments, the acid anhydride moiety comprises a moiety of Formula AA:

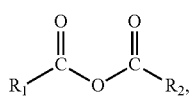

(Formula AA)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

In some embodiments, the acid anhydride moiety is a maleic acid anhydride moiety, a succinic acid anhydride moiety, or a phthalic acid anhydride moiety. In some embodiments, the acid anhydride moiety is a maleic acid anhydride (MAA) moiety of formula MAA-1:

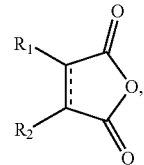

(Formula MAA-1)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

In some embodiments, the MAA moiety is the MAA moiety of Formula MAA-2:

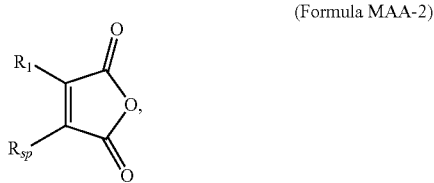

(Formula MAA-2)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_{sp}$ represents a solid support or a molecule or moiety that binds or is conjugated to a solid support (e.g., via a linker).

In some embodiments, R1 and/or R2 of formula AA, formula MAA-1, or formula (MAA-2) are, independently, hydrogen, methyl (—$CH_3$), trichloromethyl (—$CCl_3$), or trifluoromethyl (—$CF_3$).

In some embodiments, the glycoprotein is contacted with the solid support at basic pH. In some embodiments, cleaving the bond between the glycan and the polypeptide comprises contacting the glycoprotein with an endoglycosidase. In some embodiments, the endoglycosidase comprises a peptide N-glycosidase F. In some embodiments, cleaving the bond between the glycan and the polypeptide comprises contacting the glycoprotein with $O^{18}$ water. In some embodiments, cleaving the bond between the glycan and the polypeptide comprises exposing the glycoprotein to microwaves. In some embodiments, the microwaves are generated by a domestic microwave. In some embodiments, the glycan is separated from the polypeptide bound to the solid support via elution. In some embodiments, the elution is at basic or neutral pH. In some embodiments, the method further comprises releasing the bound polypeptide from the solid support. In some embodiments, the polypeptide is released from the solid support after the glycan is separated from the polypeptide. In some embodiments, the polypeptide is released from the solid support by elution at acidic pH. In some embodiments, the method is carried out under nondenaturing conditions. In some embodiments, the method further comprises digesting the polypeptide with a protease. In some embodiments, the method further comprises determining the identity of the glycan and/or the polypeptide.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DETAILED DESCRIPTION

Introduction

Figure 1:
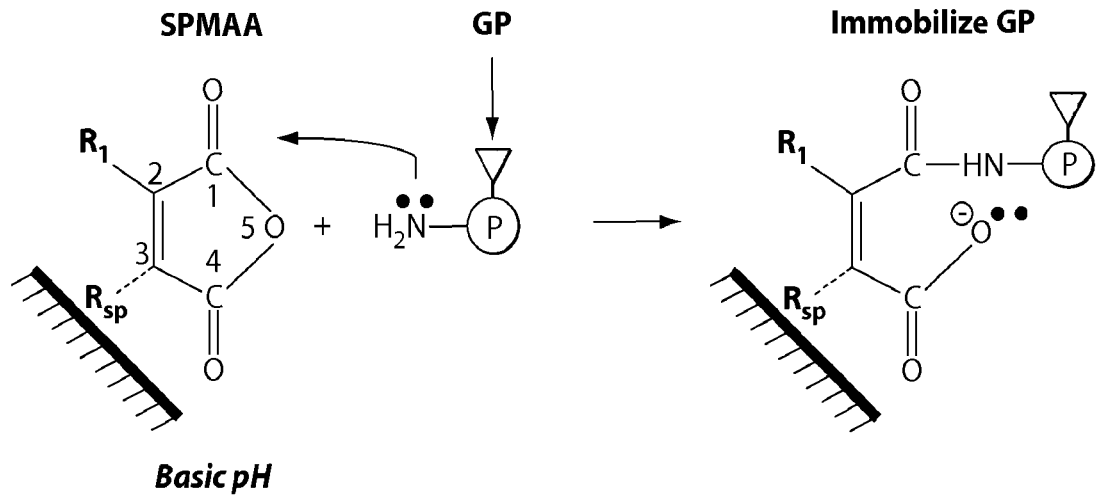
FIG. 1 illustrates an exemplary embodiment of immobilization of a glycoprotein to a solid support by covalent conjugation via anhydride chemistry.
Figure 2:
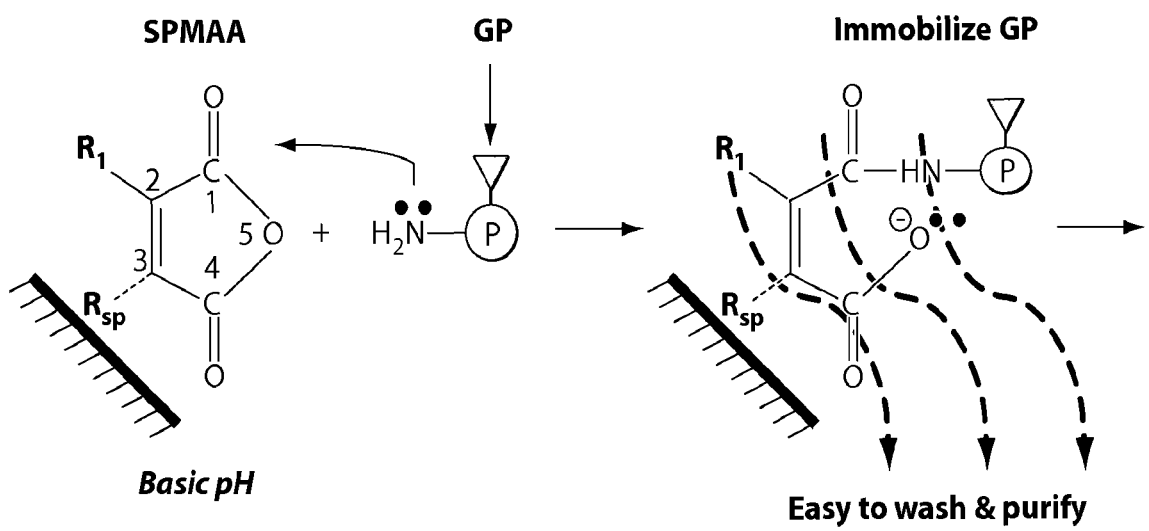
FIG. 2 illustrates an exemplary embodiment of washing and/or purifying an immobilized glycoprotein.
Figure 3:
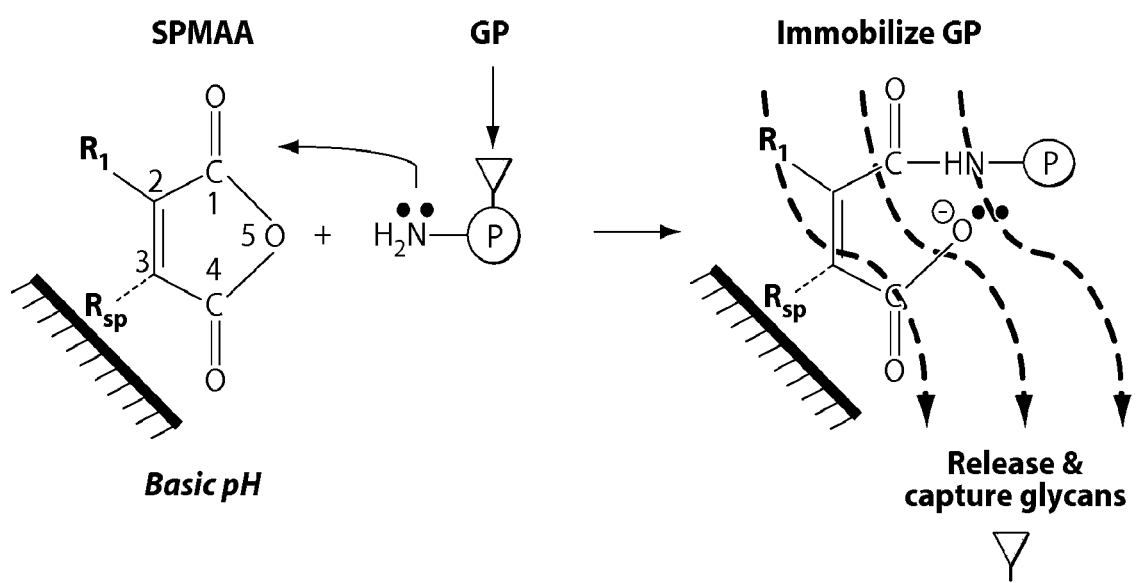
FIG. 3 illustrates an exemplary embodiment of releasing and capturing a glycan or glycan fraction from an immobilized glycoprotein.
Figure 4:
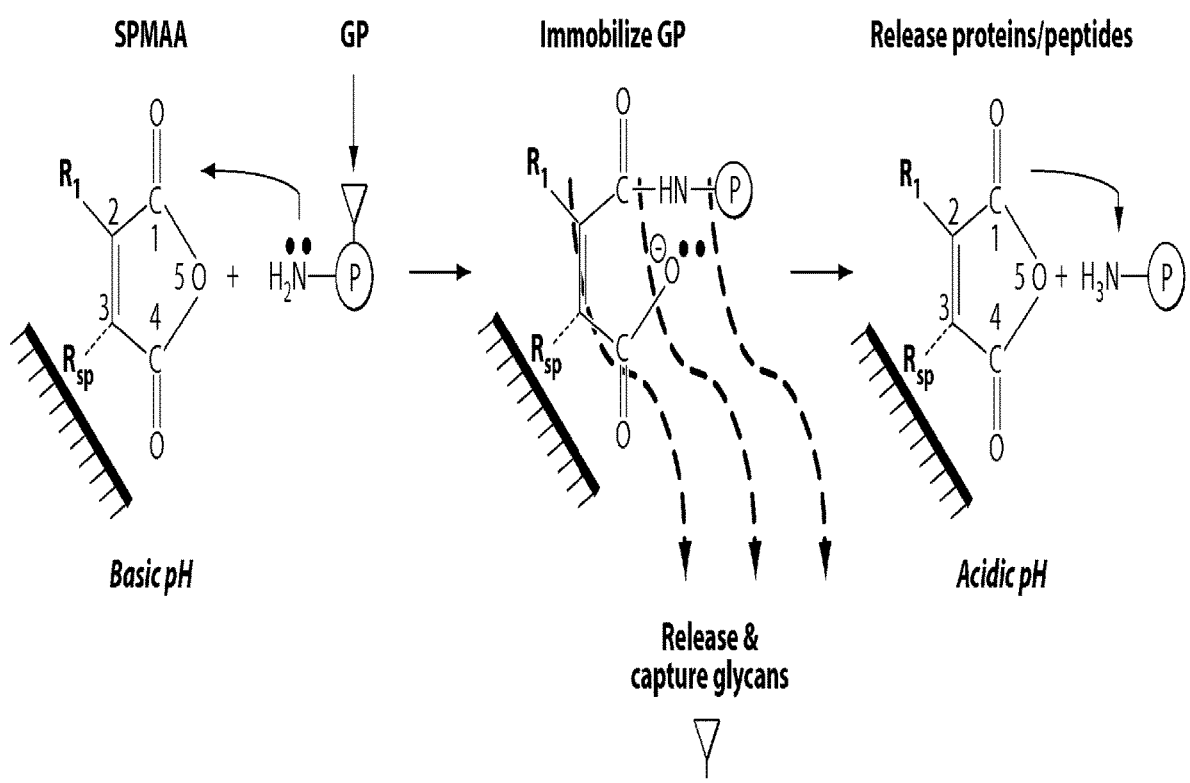
FIG. 4 illustrates an exemplary embodiment of immobilization of a glycoprotein to a solid support by covalent conjugation via anhydride chemistry, washing and/or purifying the immobilized glycoprotein, release and capture of a glycan from the immobilized glycoprotein, and release and capture of the polypeptide portion of the glycoprotein.

Glycosylation is the most abundant protein post-translational modification, playing an important role in protein folding, stability, and function. Currently established methods for glycosylation analysis do not allow for a simultaneous assessment of the protein and the glycan portion of a glycosylated protein, which is a major drawback for the investigation of glycosylation on a proteomic scale, as well as for engineering and quality control of therapeutic proteins. Based on the emerging market of protein therapeutics, e.g., therapeutic antibodies or enzymes, most of which rely on correct glycosylation for efficacy and safety, and glycoprotein-based diagnostics, there is a significant need today for improved technologies that can routinely be applied in both a clinical and a research setting for the analysis of protein glycosylation.

The term glycosylation, as used herein, refers to either (i) an enzymatic process that attaches a carbohydrate, e.g., a glycan, to a protein, lipid, or other organic molecule, or (ii) a presence of one or more glycans attached to a protein, lipid, or other organic molecule, for example, in the case of proteins, as a result of post-translational modification. Without wishing to be bound by any particular theory, it is believed that naturally occurring protein glycosylation can be a form of co-translational and post-translational modification, in that glycan addition occurs after an amino acid residue is added to the amino acid chain of a peptide or protein.

The term carbohydrate, as used herein, refers to an organic compound consisting of carbon, hydrogen, and oxygen, including, for example, monomeric sugars (monosaccharides), oligomeric sugars (oligosaccharides, e.g., disaccharides, trisaccharides, etc.), and polysaccharides. In some embodiments, the carbohydrate is a glycan. Carbohydrates generally have the molecular formula $C_nH_{2n}O_n$, but important exceptions exist, e.g., deoxyribose, a component of DNA, is a sugar of the formula $C_5H_{10}O_4$. Carbohydrates are also sometimes referred to as polyhydroxy aldehydes and ketones. Carbohydrates can comprise a single sugar moiety, or a plurality of sugar moieties, and can be classified based on the number of sugar moieties comprised into monosaccharides, disaccharides, oligosaccharides, and polysaccharides. Examples of monosaccharides include, without limitation, glucose, sucrose, galactose, mannose, ribose, arabinose, xylose, and fructose. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Naturally produced carbohydrates include N-glycans, O-glycans, monosaccharides, oligosaccharides, polysaccharides (large polymers of sugar chains e.g. cellulose), and glycolipids. N-glycans are a large and heterogeneous post-translational modification that links to the side chain of asparagine in protein backbone via a β-amide bond. Mammalian N-glycans can be enzymatically released using a universal N-glycanase: PNGase F (peptide-N4-(acetyl-β-glucosaminyl) asparagine amidase). Depending on the nature of the glycoproteins it typically takes at least several hours to perform this enzyme reaction using conventional methods. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose. (e.g., 2'-fluororibose, 2'-deoxyribose, and hexose). Carbohydrates may exist in many different forms, for example, cyclic forms, acyclic forms, stereoisomers, tautomers, anomers, and isomers.

The term glycan, as used herein, refers to a type of carbohydrate, typically an oligosaccharide or polysaccharide. Glycans typically comprise monosaccharide residues linked by O-glycosidic linkages. Glycans can be homo- or heteropolymers of monosaccharide residues, and can be linear or branched. In the context of protein glycosylation, the term glycan refers to the carbohydrate portion of a glycoprotein. In some embodiments, the term glycan refers to glycans having a molecular weight of less than about 200 kDa, less than about 150 kDa, less than about 100 kDa, less than about 50 kDa, less than about 40 kDa, less than about 30 kDa, less than about 25 kDa, less than about 20 kDa, less than about 15 kDa, less than about 10 kDa, less than about 9 kDa, less than about 8 kDa, less than about 7 kDa, less than about 6 kDa, less than about 5 kDa, less than about 4 kDa, less than about 3 kDa, less than about 2 kDa, less than about 1.5 kDa, less than about 1 kDa, or less than about 500 Da. In some embodiments, the term glycan refers to any glycan except glycosaminoglycans.

Without wishing to be bound to any particular theory, glycans are typically divided into five classes: (i) N-linked glycans are glycans attached to a nitrogen of an asparagine or arginine residue side-chain of proteins or peptides; (ii) O-linked glycans are glycans attached to the hydroxy group oxygen of a serine, threonine, tyrosine, hydroxylysine, or hydroxyproline residue side-chain of proteins or peptides, or to oxygens on lipids such as ceramide; (iii) phospho-glycans are glycans attached to the phosphate moiety of a phospho-serine residue of a protein or peptide; (iv) C-linked glycans are glycans attached to a carbon atom of a tryptophan residue side-chain; and (iv) GPI anchors are glycans linking proteins to lipids.

In contrast to the non-enzymatic, chemical reaction of protein glycation, protein glycosylation is an enzyme-mediated, site-specific process, in which specific glycan chains are added to a specific residue of a specific protein by the respective glycosyl transferase enzyme. Glycosylation can significantly change the physical and functional properties of a protein, and defective or aberrant glycosylation may result in a loss of function of a given protein. Further, differential glycosylation increases protein diversity in the proteome, because almost every aspect of glycosylation can be varied, including the site of glycan linkage, e.g., the amino residue of a protein to which a given glycan chain is attached; glycan composition (e.g., the type of sugars comprised in a given glycan chain); glycan structure (e.g., branched or unbranched); and glycan chain length (e.g., short- or long-chain oligosaccharides).

The term protein is used herein interchangeably with the term polypeptide, and refers to a polymer of amino acid residues linked together by peptide bonds. The term, as used herein, refers to proteins, polypeptides, and peptides of any size, structure, or function. A protein may be a naturally occurring protein, a fragment of a naturally occurring protein, or an engineered protein, for example, a recombinant protein, or a protein in which one or more amino acid residues are non-naturally occurring residues, e.g., modified amino acid residues, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex.

The term glycoprotein, as used herein, refers to a glycosylated protein. Accordingly, a glycoprotein comprises a polypeptide portion, typically a linear amino acid sequence or a complex of two or more linear amino acid sequences, and a glycan portion, e.g., one or more glycan molecules that are covalently bound to the polypeptide portion of the glycoprotein.

Protein glycosylation serves a variety of structural and functional roles, for example, in membrane and secreted proteins, and the majority of proteins synthesized in the rough ER undergo glycosylation. Glycosylation is also present in the cytoplasm and nucleus as the O-GlcNAc modification. Protein glycosylation plays a role in protein folding and stability. Some proteins do not fold correctly unless they are glycosylated first. Glycans have been reported to modulate protein half-life, e.g., some glycans confer stability to secreted glycoproteins which are rapidly degraded in the absence of correct glycosylation. Glycosylation also plays a role in cell-cell adhesion, e.g., via sugar-binding proteins such as lectins, which recognize specific glycan moieties on specific cell surface glycoproteins.

Protein glycosylation is an important aspect in the development of therapeutic proteins and peptides, as many protein therapeutics that are developed or already approved are glycosylated and correct glycosylation is important or essential for therapeutic efficacy. For example, glycan composition and structure play a critical and key role in therapeutic antibody and antibody fragment efficacy and safety. Human antibodies have a conserved glycosylation site at Asn-297. Correct glycosylation at Asn-297 has been reported to be essential for therapeutic antibody function, and subtle changes in glycosylation structure have been linked to significant safety issues (see, e.g., Walsh, *Biopharmaceutical benchmarks* 2010 Nature Biotechnology 28, 917-924 (2010); Anthony, *Recapitulation of IVIG anti-inflammatory activity with a recombinant IgG Fc.* Science. 2008 Apr. 18; 320(5874):373-6; and Bosques, *Chinese hamster ovary cells can produce galactose-α-1,3-galactose antigens on proteins* Nature Biotechnology 28, 1153-1156 (2010); the entire contents of each of which are incorporated herein by reference).

It is important for therapeutic protein approval and production that proteins are produced with the correct glycosylation pattern and that precise quality control measures are implemented to assure correct glycosylation, for example, to avoid loss of efficacy and detrimental effects in the case of aberrant glycosylation. In order to obtain correctly glycosylated peptide or protein therapeutics, mammalian cell lines are often required for their production, since bacterial, yeast, or insect cells often cannot produce the complex glycans and/or glycosylation patterns required for proper protein function.

The term solid support is used herein interchangeably with the term solid phase, and refers to a water-insoluble substance which is in a solid state under physiological conditions. In some embodiments, the term solid support refers to a substance which is in a solid state under physiological conditions and under conditions that are encountered during the steps of a method described herein, e.g., within the range of pH values used in the steps of immobilizing and releasing a protein to and from a solid support described herein. In some embodiments, the solid support takes the form of a bead, a resin, a gel, a membrane, a filter, or a vessel surface (e.g., the surface of a culture vessel or a test tube). A solid support may comprise a single type of material, e.g., a single polymeric material, or a plurality of different materials, e.g., a copolymer. Non-limiting examples of suitable solid support materials include various plastics, glasses, gels, and clays. In some embodiments, the solid support comprises or consists of a polymer, for example, an organic polymer or an organic copolymer, of $SiO_2$, or of $Al_2O_3$. Suitable polymers and copolymers include, without limitation, e.g., polycarboxylic acid polymers and copolymers, including polyacrylic acids; acetal polymers and copolymers; acrylate and methacrylate polymers and copolymers (e.g., n-butyl methacrylate); cellulosic polymers and copolymers, including cellulose, modified cellulose, cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyl resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropr-opene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), polyoxypropylenes, PLURONIC™ family of block copolymers including PLURONIC® F68, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85, polyoxyethylene (polyethylene glycol), polyanhydrides, polyvinylalcohol, polyethyleneamine and polypyridine, as well as blends and copolymers of the above. The polymers and copolymers may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (e.g., arborescent and hyperbranched polymers). The polymers can be formed from a single monomer (e.g., they can be homopolymers), or they can be formed from multiple monomers (e.g., they can be copolymers) that can be distributed, for example, randomly, in an orderly fashion (e.g., in an alternating fashion), or in blocks. Additional materials suitable as solid supports in the context of this disclosure will be apparent to those of skill in the art. The disclosure is not limited in this respect.

The term solid-phase acid anhydride refers to an acid anhydride moiety that is conjugated to a solid support. Accordingly, the term solid-phase maleic acid anhydride (SPMAA), as used herein, refers to a maleic acid anhydride moiety that is conjugated to a solid support. The conjugation may be, for example, by direct covalent bond, or via a linker.

The term conjugated or conjugation refers to an association of two entities, for example, of two molecules such as a solid support and a proteins, a solid support and a reactive moiety, e.g., an anhydride moiety, or a glycan to a protein via a covalent bond. The association can be, for example, via a direct or indirect (e.g., via a linker) covalent linkage or via non-covalent interactions. In some embodiments, the association is covalent. In some embodiments, two molecules are conjugated via a linker connecting both molecules. In some embodiments, conjugation of a protein, e.g., a glycoprotein, to a solid support leads to immobilization of the conjugated protein on the solid support.

The term surface, as used herein in the context of materials, e.g., of solid support materials, refers to the exterior boundary or the outermost layer of the respective material. A surface typically constitutes the interface of a material with a different material and/or a different phase. For example, a surface may be the exterior boundary of a solid material, e.g., of a bead, that is in contact with a liquid material, e.g., with a sample comprising a glycoprotein, or with a washing or elution fluid.

The term elution, as used herein, refers to the capture of molecules, e.g., of a glycan portion or of a protein portion of an immobilized glycoprotein, in a liquid phase. In some embodiments, the elution involves contacting a solid support on which a molecule is immobilized with an elution fluid, e.g., water, acid, or a buffer, incubating the solid support contacted with the elution fluid for a time and under conditions suitable for the molecule to be captured in the elution fluid, and then physically separating the elution fluid from the solid support, e.g., by gravity, centrifugation, magnetic separation, or any other suitable method. For example, an elution of a protein covalently bound to an SPMAA via an $NH_2$-acid anhydride bond, can be eluted from the SPMAA by contacting the SPMAA with an elution fluid that releases the bound protein from the SPMAA, e.g., an elution fluid comprising an acid or a buffer at acidic pH, or a protease, and subsequently separating the elution fluid from the SPMAA, e.g., by centrifugation.

Strategies, Methods, and Reagents for Glycoproteomics

Some aspects of this disclosure provide methods for separating and/or isolating a glycan from a glycoprotein comprising the glycan bound to a polypeptide. In some embodiments, the method comprises contacting the glycoprotein with a solid support that binds the polypeptide, cleaving a bond between the glycan and the polypeptide, and separating the glycan from the polypeptide. In some embodiments, the method further comprises isolating the glycan and/or the polypeptide. In some embodiments, the binding of the solid support to the polypeptide is unbiased binding.

The term separation, as used herein, refers to a physical separation of an entity, e.g., a molecule or a class of molecules, from another entity, e.g., another molecule or class of molecules, or a mixture of entities. For example, a fractionation of a mixture of molecules by molecular weight results in the separation of molecules below the molecular weight cutoff from those above the molecular weight cutoff. Separation does not necessarily require purification, but a purification typically includes a separation of the entity to be purified from any unwanted entities.

The term isolation, as used herein, refers to the removal, through human intervention, of a molecule, for example, a carbohydrate or a polypeptide, from a component, e.g., another molecule or a class of molecules with which it is associated in nature, or, in the case of non-naturally occurring molecules, with which it is associated when originally produced. In some embodiments, the removal may be by separation of the molecule from the component. In other embodiments, the removal may be by a destruction of an association between the molecule and the component, or by a destruction or conversion of the component. For example, a glycan enzymatically cleaved from a naturally occurring or engineered glycoprotein, a glycan physically separated from the polypeptide portion of a glycoprotein, a glycan left over after protease digest of a glycoprotein, and a purified glycan are non-limiting examples of what may be referred to as an isolated glycan in some embodiments.

The term purification, as used herein, refers to an increase in the concentration of a particular molecule, e.g., a glycan or a polypeptide, in a sample. In some embodiments, purification entails an increase of the abundance of the molecule in the sample to more than 10%, more than 20%, more than 30%, more than 40%, more than 50%, more than 60%, more than 70%, more than 80%, more than 90%, more than 95%, more than 98%, more than 99%, more than 99.5%, or more than 99.9% of the molecule of its class, or of all molecules, or all molecules other than a solvent or excipient in the sample.

Some aspects of this disclosure relate to the recognition that one major roadblock to efficient glycosylation analysis, for example, in the context of glycoproteomic research, diagnostic biomarker discovery, and therapeutic protein production and quality control is that current methods do not allow the isolation and analysis of both the purified glycan portion and the protein portion of glycoprotein molecules from a single sample. Current methods for glycoprotein analysis, include, but are not limited to, C18-SPE, PGC-SPE, organic solvent precipitation, size-based gel chromatography, NIBRT glycomics, and prozyme glycoprep. The current methods are burdened by a host of drawbacks, which hamper their broad application to glycoproteomics. For example, existing methods do not allow for the capture of both protein and glycan portions of a given glycoprotein. Separation and isolation of glycans from glycoproteins is also typically associated with cumbersome, time consuming and complex purification procedures, and current methods are generally limited to specific glycans, or specific proteins, making unbiased capture of glycans and/or proteins from a glycoprotein sample impractical. Additionally, current methods typically require extensive sample handling, which is associated with significant protein/glycan loss and/or damage, limiting the application of these methods to scenarios where large amounts of starting material is readily available.

For example, some affinity chromatography based methods do not allow for complete elution of pure and intact protein/peptide and/or glycan, and are often burdened by poor recovery, making them impractical in many applications. Additionally, in many of the current methods, contaminating glycan or peptide/protein must be purified out in an additional step and the data must be adjusted to account undesired cross-contamination. Further, under some circumstances, the elution volume can require evaporative techniques that take days before the additional purification steps can be performed. Another drawback is that, typically, current methods cannot easily be scaled up, for example, from a single glycoprotein to a plurality of glycoproteins, or from laboratory to production scale, and are so time- and cost-intensive to the point that broad applications in clinical or research settings are impractical. The technology described herein overcomes these drawbacks of existing methods.

Some aspects of this disclosure provide a technology that allows separation and/or isolation of the glycan portion and/or the polypeptide portion of a glycoprotein. In general, the methods for separating and/or isolating a glycan from a glycoprotein comprising the glycan bound to a polypeptide described herein involve contacting the glycoprotein with a solid support that binds the polypeptide, cleaving a bond between the glycan and the polypeptide, and separating the glycan from the polypeptide. In some embodiments, the method also involves isolating the glycan and/or the polypeptide.

The instantly disclosed technology allows for the efficient separation and isolation of glycans from glycosylated proteins, also referred to herein as glycoproteins, without losing the polypeptide portion of the glycosylated proteins. The protein portion can be isolated as well, from the same glycoprotein, which allows isolation of glycan and polypeptide portion of a glycoprotein from a biological sample via a single method. Both glycan and polypeptide portions can subsequently be subjected to further analysis. One important advantage of the technology described herein over current technologies is that it allows for an unbiased isolation of glycans and polypeptides from glycoproteins, making it particularly useful for applications in which isolation bias is detrimental, such as glycomics and proteomics applications.

Some aspects of this disclosure relate to the surprising discovery that glycoproteins can efficiently be immobilized on solid supports by an appropriate chemistry on the surface of the solid support. For example, as described herein, a glycoproteins comprised in a biological sample can be immobilized on a solid support, e.g., a bead, that comprises a reactive moiety reacting with the N-terminal amino group of the polypeptide chain of the glycoprotein, e.g., an anhydride moiety. Some aspects of this disclosure relate to the surprising discovery that the immobilization of the glycoprotein according to the methods described herein is stable enough to allow for the release of a glycan from the glycoprotein, e.g., by cleaving a covalent bond that links the glycan to the polypeptide, or by cleaving a bond within the glycan portion of the glycoprotein, which releases a partial glycan structure from the glycoprotein. Some aspects of this disclosure relate to the surprising discovery that the immobilization of the glycoprotein according to the methods disclosed herein can be reversed under conditions that allow for the recovery of the immobilized polypeptide portion of the glycoprotein, e.g., of the intact polypeptide portion of the glycoprotein.

In some embodiments, methods, devices, and reagents are provided that allow for the separation and/or isolation of either or both the glycan and protein portions comprised in a glycoprotein. The disclosure provides methods, devices, and reagents for the immobilization of a glycoprotein to a solid support, for the release of a glycan from a glycoprotein, e.g., from an immobilized glycoprotein, for the separation and/or isolation of the glycan portion, and for the release and/or isolation of the deglycosylated polypeptide portion of the glycoprotein.

The technology described herein can be employed for the separation and/or isolation of glycan and polypeptide portions of glycoproteins of various types and from various sources, including, but not limited to, from compositions comprising a single glycoprotein; and from compositions comprising a plurality of glycoproteins, for example, from a biological sample comprising a plurality of glycoproteins, such as body fluid sample (e.g., blood, serum, plasma, urine, lymph fluid, synovial fluid, cerebrospinal fluid, saliva, sweat, tears, interstitial fluid, ascites fluid, etc.) obtained from a subject, or a tissue sample, e.g., a biopsy sample, obtained from a subject.

The methods and strategies for separating and/or isolating the glycan and/or the polypeptide portion of a glycoprotein described herein can be applied to any glycoprotein. In general, the glycan and the protein to be separated and/or isolated are comprised in a glycoprotein. In some embodiments, the glycan and the protein portion of the glycoprotein are conjugated via a covalent bond. In some embodiments, the method comprises releasing the glycan from the glycoprotein after immobilization of the glycoprotein to a solid support. In some embodiments, the releasing of the glycan comprises breaking or cleaving a covalent bond between the glycan and the protein portion of the glycoprotein. In some embodiments, the covalent bond is cleaved by an enzyme. In some embodiments, a glycan covalently bound to a protein portion of a glycoprotein is released from the glycoprotein by contacting the glycoprotein with an enzyme that cleaves a covalent bond between the glycan and the polypeptide portion of the glycoprotein. In some embodiments, the method comprises contacting the glycoprotein with an endoglycosidase. In some embodiments, the endoglycosidase comprises an N-glycanase (e.g., peptide N-glycosidase F, endoglycosidase H, endoglycosidase Hf, and/or peptide N-glycosidase A), an O-glycosidase or O-glycanase, or with an exoglycosidase. In some embodiments, a glycan is released from a glycoprotein by cleaving a covalent bond between the glycan and the protein portion via base elimination. In some embodiments, glycan release via base elimination comprises contacting a glycoprotein with a base, for example, NaOH or KOH, ammonia, dimethylamine, trimethylamine, etc., in an amount sufficient to create a pH equal to or greater than 11. In some embodiments, release of a glycan from a glycoprotein comprises exposing the glycoprotein to a source of energy, for example, to heat or microwave energy, as described in more detail elsewhere herein.

In some embodiments, the glycan is selected from the group consisting of an O-glycan and an N-glycan. In some embodiments, the glycan is bound to the polypeptide via an amino group of an Asparagine residue comprised in the polypeptide. In some embodiments, the glycan is bound to the polypeptide via a hydroxyl group of a serine or threonine residue comprised in the polypeptide. In some embodiments, the bond is a covalent bond. In some embodiments, the cleaving of the bond comprises contacting the glycoprotein with a glycosidase. In some embodiments, the glycosidase comprises an endoglycosidase. In some embodiments, the glycosidase comprises an exoglycosidase. In some embodiments, the glycosidase comprises one or more endoglycosidases selected from the group comprising peptide N-glycosidase F, endoglycosidase H, endoglycosidase Hf, peptide N-glycosidase A, and O-glycanase. In some embodiments, the cleaving of the bond comprises base elimination. In some embodiments, the cleaving of the bond comprises exposing the glycoprotein to microwaves. In some embodiments, the microwaves are generated by a domestic microwave device.

In some embodiments, a sub-moiety glycan is released, separated, and/or isolated. The term sub-moiety glycan refers to a carbohydrate that constitutes part of an intact glycan. For example, in an intact glycan comprising a plurality of monosaccharides linked together, each monosaccharide or each moiety comprising some but not all monosaccharide units comprised in the glycan would be sub-moiety glycans. In some embodiments, a sub-moiety glycan comprises at least 2, at least 3, at least 4, or at least 5 monosaccharide units. In some embodiments, the intact glycan can be determined by analyzing a sub-moiety glycan released from it.

In some embodiments, the method comprises separating the glycan portion released from a glycoprotein. In some embodiments, the method comprises capturing the glycan portion of the polypeptide. In some embodiments, the method comprises capturing the de-glycosylated polypeptide portion of the glycoprotein. In some embodiments, the method further comprises fragmenting the polypeptide. In some embodiments, the fragmenting comprises digesting the polypeptide with a protease. In some embodiments, the method comprises isolating the glycan separated from the polypeptide. In some embodiments, the method comprises isolating the polypeptide separated from the glycan. In some embodiments, the method further comprises analyzing the glycan and/or the polypeptide after the separating. In some embodiments, analyzing comprises subjecting the glycan and/or the polypeptide to high performance liquid chromatography, capillary electrophoresis, and/or mass spectrometry. In some embodiments, the method further comprises modifying or labeling the polypeptide or the glycan. In some embodiments, the labeling comprises permethylation or fluorophore labeling. In some embodiments, the fluorophore labeling comprises 2-AA (2-aminobenzoic acid (anthranilic acid)) or 2-AB (2-aminobenzamide) labeling.

The methods provided herein allow for the unbiased immobilization and processing of glycoproteins. For example, in some embodiments, a solid support is used that forms a covalent bond with an amino group (an $NH_2$ group). If such a solid support is contacted with a molecule comprising an $NH_2$ group under suitable conditions, the molecule is bound and immobilized on the solid support. In some embodiments, a solid support comprising an anhydride moiety is employed to bind and immobilize proteins. As all proteins have a primary $NH_2$ group, either in the side chain of a lysine residue or at the N-terminus of the amino acid chain, all proteins can be bound by an $NH_2$-reactive moiety, e.g., an anhydride moiety, conjugated to the solid support.

The immobilization of a glycoprotein on the surface of a solid support, e.g., of a bead, membrane, resin, or test tube surface, eliminates some of the constraints or limitations that are classically associated with liquid phase reactions because the glycoprotein is converted from a state that is freely mobile within the liquid phase to a quasi-solid state. It will be understood that the methods and strategies described herein are not limited to soluble proteins, but can also be applied to insoluble proteins, anchored proteins, membrane proteins, and protein aggregates.

In some embodiments, the glycan portion of a glycoprotein immobilized to a solid support according to methods provided herein is released from the glycoprotein. The released glycan portion can then be readily separated from the immobilized glycoprotein, irrespective of their size, structure, acidity or alkalinity, or their hydrophilicity. The de-glycosylated polypeptide portion of the immobilized glycoprotein can also be released from the solid support and captured without a bias for size, structure, acidity or alkalinity, or their hydrophilicity. Accordingly, the methods provided herein allow for the unbiased assessment of glycoprotein populations, e.g., populations of different glycoproteins in a complex biological sample, e.g., a body fluid sample.

In some embodiments, an anhydride chemistry is used to immobilize a glycoprotein to the surface of a solid support. For example, in some embodiments, a glycoprotein is immobilized on a solid support comprising or conjugated to an anhydride moiety, e.g., a maleic acid anhydride moiety, a succinic acid anhydride moiety, or a phthalic acid anhydride moiety that is conjugated to the solid support. Typically, immobilization of a protein to a solid support via anhydride chemistry involves contacting the solid support comprising the anhydride moiety with the protein under conditions of basic pH, e.g., at a pH of at least 7, at least 7.5, least 8, at least 8.5, at least, 9, at least 9.5, at least 10, at least 10.5, at least 11, at least 11.5, or at least 12, at a pH of 7-9, at a pH of 8-12, at a pH of 9-12, at a pH of 10-12, at a pH of about 8.5, about 9, about 9.5, about 10, about 10.5, about 11, about 11.5, or at a pH of about 12.

In some embodiments that use anhydride chemistry to immobilize a glycoprotein, e.g., maleic acid anhydride, succinic acid anhydride, or phthalic acid anhydride chemistry, the immobilization is reversible. For example, a glycoprotein or a de-glycosylated polypeptide portion of a glycoprotein immobilized to a solid support via anhydride chemistry can be released by contacting the solid support with an acidic solution, which uncouples the anhydride-$NH_2$ covalent bond and restores the anhydride moiety on the solid support. In some embodiments, the acidic solution is at a pH of less than 7, less than 6.5, less than 6, less than 5.5, less than 5, less than 4, less than 3, less than 2, or less than 1, at a pH of 1-5, at a pH of 1-4, at a pH of 1-3, at a pH of 1-2, at a pH of 2-5, at a pH of 2-3, at a pH of 2-4, at a pH of about 1, at a pH of about 2, at a pH of about 2.5, at a pH of about 3, at a pH of about 3.5, at a pH of about 4, at a pH of about 4.5, or at a pH of about 5. In some embodiments, the release of the immobilized glycoprotein, or of an immobilized, de-glycosylated polypeptide portion of a glycoprotein, is enhanced by an increased temperature, e.g., by incubation of the solid support at an acidic pH at a temperature of 30° C.-72° C., e.g., at a temperature of about 30° C., about 31° C., about 32° C., about 33° C., about 34° C., about 35° C., about 36° C., about 37° C., about 38° C., about 39° C., about 40° C., about 41° C., about 42° C., about 45° C., about 50° C., about 55° C., about 60° C., about 70° C., or about 72° C. In some embodiments, incubation at a temperature of more than 72° C. is used to enhance release of an immobilized protein.

In some embodiments, the combination of acidic conditions and high temperature for releasing an immobilized protein from a solid support as described herein results in a rapid decoupling without or with only minimal side reactions. The temperature used for decoupling a given immobilized protein or population of proteins will typically be chosen to allow for a balance of rapid release of the protein while minimizing protein heat denaturation. The optimal release temperature may also depend on the type of solid support and by the specific surface chemistry chosen, but is typically irrespective of the properties of the proteins to be released (e.g., size, hydrophobicity, high-order structures, type (e.g., membrane or secreted), or solubility). Without wishing to be bound by any particular theory, it is believed that essentially all types of proteins exhibit the same or similar decoupling performance in the context of immobilization via anhydride chemistry and that the different amino acid side chain composition of different proteins or other groups comprised in the protein will not affect the release kinetics.

In some embodiments, a protein or polypeptide immobilized to a solid-phase acid anhydride as described herein, e.g., an SPMAA-immobilized protein or polypeptide, may be released from the solid support by hydrolyzing a peptide bond within the peptide, e.g., by exposing the immobilized protein or polypeptide to a protease or other peptide-bond-cleaving conditions. In some such embodiments, the released protein or polypeptide is a fragment of the immobilized protein or polypeptide.

While the methods and strategies for separating glycan and polypeptide portions of glycoproteins can be used to immobilize and process glycoproteins in an unbiased manner, the disclosure is not limited in this respect. For example, in some embodiments, the disclosure provides methods and strategies for the selective immobilization and processing of specific glycoproteins or for the release of specific glycan portions from a glycoprotein.

For example, in some embodiments, methods are provided for the release and capture of O-glycosylation moieties from glycoproteins. Currently available methods for the release and capture of O-glycans from glycoproteins typically include treatment of the glycoproteins with a basic solution (e.g., NaOH, pH>11), which typically results in the hydrolysis of some amide bonds among the protein backbone. Accordingly, larger glycoproteins of interest may be hydrolyzed into several segments by this treatment, which makes subsequent analyses of a captured polypeptide portion difficult or impossible in the context of liquid phase methodologies. The methods and strategies for glycosylation analysis described herein, in contrast, allow for the quantitative capture of all protein fragments created by basic hydrolyzation, because the resulting $NH_2$ groups will react with the reactive moieties of the solid support, thus immobilizing any hydrolyzation fragments on the solid support. Accordingly, such hydrolyzation segments are not lost when the instantly disclosed solid-phase immobilization methods are used, and can be released from the solid support and subsequently be captured and analyzed.

In some embodiments, methods and strategies for separating glycan and polypeptide portions of glycoproteins are used to immobilize and process glycoproteins comprised in a complex sample, e.g., a complex biological sample, such as a body fluid or biopsy sample obtained from a subject, or a cell culture supernatant or crude cell lysate sample. Biological samples typically contain significant amounts of molecules other than glycoproteins, e.g, nucleic acids such as DNA and RNA, lipids, and metabolites. While some of these molecules may be depleted in a sample by physical separation, e.g., by size fractionation methods, some of these molecules may have a molecular weight comparable to that of the glycoprotein(s) of interest in the sample. The methods and strategies for glycoprotein immobilization described herein have the advantage that most of these non-target molecules do not contain a primary —$NH_2$ group and, thus, are not immobilized by the methods described herein that use an anhydride chemistry, but remain in solution while the glycoproteins of interest are immobilized. The non-target molecules can thus be readily removed after the immobilization of the glycoprotein(s) of interest in the sample, for example, by washing of the solid support with an appropriate wash buffer.

For example, in some embodiments, a body fluid sample, e.g., a urine or blood sample, is obtained from a subject. The sample is contacted with a solid support comprising an anhydride moiety under basic pH conditions. While glycoprotein(s) in the sample are immobilized as a result of the formation of a covalent bond between the anhydride of the solid support and the $NH_2$ group(s) of the protein(s), other components of the body fluid sample, e.g., metabolites, lipids, carbohydrates, nucleic acids, salts, etc., can be easily removed, for example, by washing the solid support with a wash buffer.

Even if some non-target molecules are immobilized by the anhydride chemistry of the solid support, e.g., molecules that are not glycoproteins but still contain an amino group, they can typically be separated from the polypeptide fraction after release from the solid support, e.g., by size fractionation or other separation techniques known to those of skill in the art. In some embodiments, de-glycosylated polypeptides can be distinguished from polypeptides that were immobilized on the solid support, but did not comprise a glycan portion, by selective labeling of those polypeptides that comprise a glycan or that were de-glycosylated. This can be achieved by various strategies known to those of skill in the art. One suitable approach is, for example, to contact the immobilized glycoproteins with $O^{18}$ water and a glycosidase for de-glycosylation, which results in incorporation of an $O^{18}$ atom into the polypeptide at the de-glycosylation site. Polypeptides derived from glycoproteins are thus marked by an $O^{18}$ label, which can be detected by methods known to those of skill in the art, e.g., by mass spectrometry.

In some embodiments, a sample comprising glycoproteins and non-glycosylated proteins may be pre-processed to enrich for glycoproteins or to deplete non-glycosylated proteins from the sample, e.g., by chromatography methods (e.g., hydrophilic interaction chromatography (HILIC)), or by lectin-based chromatography.

In some preferable embodiments, the glycoprotein(s) to be immobilized is a soluble glycoprotein. However, the methods provided herein are not limited to soluble proteins, as insoluble, aggregated, or dispersed proteins may also be subjected to the methods and strategies for glycosylation analysis provided herein. In some such embodiments, the insoluble, aggregated, or dispersed protein are solubilized prior to immobilization, e.g., by methods known to those of skill in the art. For example, in some embodiments, an insoluble glycoprotein is solubilized by contacting is with a solubilizing agent, e.g., with SDS or urea, in aqueous solution in an amount or at a concentration effective to solubilize the protein. The solubilized protein can then be contacted to the solid support comprising a reactive moiety for immobilization. Once immobilized, the solubilizing agent, e.g., the urea or SDS, can be washed away from the solid support, leaving behind the immobilized protein, which can then be subjected to the glycan release and capture steps as well as the subsequent polypeptide release and capture steps described herein.

The ability to immobilize an insoluble protein and then wash away the solubilizing agent before further processing, e.g., before the release and capture of the glycan portion from the immobilized glycoprotein, constitutes another advantage of the methods and strategies described herein over currently used liquid phase methodology. For example, some enzymes that are useful for the release of glycans from glycoproteins, e.g., PNGase F, are sensitive to denaturation and loss of function in the presence of commonly used solubilizing agents, such as SDS or urea, and are thus incompatible with the presence of such agents. Accordingly, it is technically difficult or impossible to use such sensitive enzymes on some insoluble proteins or protein fractions in the context of liquid phase methodologies. For example, under some circumstances, the undesirable effects of urea and SDS may be mitigated by addition of the detergent NP-40 to some extent, which may allow limited access to the proteoglycome for de-glycosylating enzymes. In such cases, however, e.g., if de-N-glycosylation is carried out in liquid phase methods in the presence of SDS and NP-40, extra purification steps have to be employed to remove these molecules from the released glycans, and these purification steps are often time- and labor intensive. In contrast, the methods described herein that rely on the immobilization of glycoproteins to solid supports, e.g., to beads, create two-phases upon protein immobilization: the solid-phase (immobilized proteins on solid support), and the liquid phase, which can contain de-glycosylating enzymes, such as PNGase F. In the bi-phasic systems so created, the distribution pattern and accessibility of the glycan moieties comprised in the glycoproteins are mostly dependent on the properties of the solid support and the surface chemistry employed, but not on the solubility of the respective glycoprotein(s). Therefore, the methods and strategies described herein that involve immobilization of a glycoprotein for subsequent release and capture of the glycan and/or the polypeptide portion comprised therein are applicable to soluble and insoluble proteins, for example, of soluble and insoluble proteins of biological samples, such as urine, blood, serum, plasma, ascites fluid, cell culture supernatant, or cell or tissue lysates.

Some aspects of this invention are based on the surprising discovery that the use of an appropriate chemistry for solid-phase immobilization of proteins can be exploited to reversibly immobilize the polypeptide portion of a glycoprotein to a solid support with a bond that is stable enough to withstand reaction conditions used to release the glycan portion of the glycoprotein, but can be cleaved under conditions that allow for the release of the polypeptide portion of the immobilized glycoprotein in an intact state. In some embodiments, the immobilization is effected via an acid anhydride chemistry, e.g., via acid anhydride moieties conjugated to a solid support used as the immobilization substrate for the glycoproteins of interest. In some embodiments, the acid anhydride moiety comprises a moiety of Formula AA:

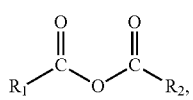

(Formula AA)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

The structure or formula AA is typically conjugated to a solid support, e.g., via a covalent bond to $R_1$ or $R_2$. In some embodiments, $R_1$ and/or $R_2$ of formula AA are, independently, hydrogen, methyl (—$CH_3$), trichloromethyl (—$CCl_3$), or trifluoromethyl (—$CF_3$).

In some embodiments, the acid anhydride moiety is a maleic acid anhydride moiety, a succinic acid anhydride moiety, or a phthalic acid anhydride moiety. Exemplary structure diagrams of these three moieties are provided below:

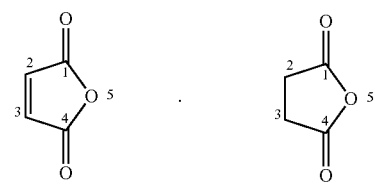

Maleic acid anhydride (MAA)    Succinic acid anhydride (SAA)

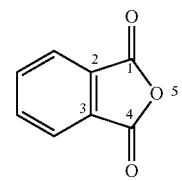

Phthalic acid anhydride (PAA)

Derivatives of the acid anhydride moieties described herein are also useful in the context of some embodiments of this disclosure, and are, accordingly, used as reactive moieties conjugated to a solid support, e.g., a bead, resin, membrane, or surface, in some embodiments.

In some embodiments, the acid anhydride moiety is a maleic acid anhydride (MAA) moiety of formula MAA-1:

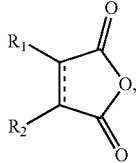

(Formula MAA-1)

wherein

∥ represents a C═C double bond $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; ═O; —C(═O)$R_A$; —$CO_2R_A$; —CN; —SCN; —$SR_A$; —$SOR_A$; —$SO_2R_A$; —$NO_2$; —$N(R_A)_2$; —NHC(O)$R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; ═O; —C(═O)$R_B$; —$CO_2R_B$; —CN; —SCN; —$SR_B$; —$SOR_B$; —$SO_2R_B$; —$NO_2$; —$N(R_B)_2$; —NHC(O)$R_B$; or —$C(R_B)_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

In some embodiments, the MAA moiety is the MAA moiety of Formula MAA-2:

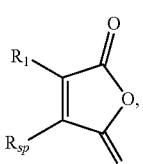

(Formula MAA-2)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; ═O; —C(═O)$R_A$; —$CO_2R_A$; —CN; —SCN; —$SR_A$; —$SOR_A$; —$SO_2R_A$; —$NO_2$; —$N(R_A)_2$; —NHC(O)$R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_{sp}$ represents a solid support or a molecule or moiety that binds or is conjugated to a solid support (e.g., via a linker).

In some embodiments, R1 and/or R2 of formula MAA-1, or formula MAA-2 are, independently, hydrogen, methyl (—$CH_3$), trichloromethyl (—$CCl_3$), or trifluoromethyl (—$CF_3$).

In some embodiments, the acid anhydride moiety is a succinic acid anhydride (SAA) moiety of formula SAA-1:

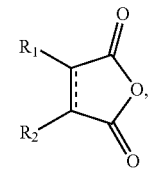

(Formula SAA-1)

wherein

∥ represents a C—C single bond;

$R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; ═O; —C(═O)$R_A$; —$CO_2R_A$; —CN; —SCN; —$SR_A$; —$SOR_A$; —$SO_2R_A$; —$NO_2$; —$N(R_A)_2$; —NHC(O)$R_A$; or —$C(R_A)_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; ═O; —C(═O)$R_B$; —$CO_2R_B$; —CN; —SCN; —$SR_B$; —$SOR_B$; —$SO_2R_B$; —$NO_2$; —$N(R_B)_2$; —NHC(O)$R_B$; or —$C(R_B)_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

In some embodiments, the SAA moiety is the SAA moiety of Formula SAA-2:

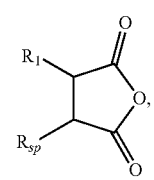

(Formula SAA-2)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_{sp}$ represents a solid support or a molecule or moiety that binds or is conjugated to a solid support (e.g., via a linker).

In some embodiments, R1 and/or R2 of formula SAA-1, or formula SAA-2 are, independently, hydrogen, methyl (—CH$_3$), trichloromethyl (—CCl$_3$), or trifluoromethyl (—CF$_3$).

In some embodiments, the acid anhydride moiety is a phthalic acid anhydride (PAA) moiety of formula PAA-1:

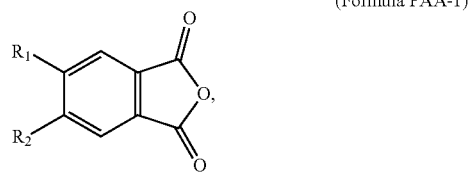

(Formula PAA-1)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

In some embodiments, the PAA moiety is the PAA moiety of Formula PAA-2:

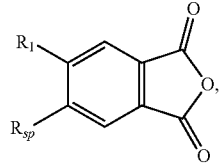

(Formula PAA-2)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_{sp}$ represents a solid support or a molecule or moiety that binds or is conjugated to a solid support (e.g., via a linker).

In some embodiments, R1 and/or R2 of formula PAA-1, or formula PAA-2 are, independently, hydrogen, methyl (—CH$_3$), trichloromethyl (—CCl$_3$), or trifluoromethyl (—CF$_3$).

While some exemplary acid anhydride moieties suitable for the use as reactive moieties conjugated to a solid support in the context of methods and strategies described herein are provided, additional suitable acid anhydride moieties will be apparent to those of skill in the art. The disclosure is not limited in this respect. While virtually any acid anhydride moiety can be used to effect the reversible protein immobilization described herein, acid anhydrides comprising the acid anhydride moiety in a five-membered ring are particularly useful in the context of reversible protein immobilization as described herein, because the energy contained in the five membered ring is also important for the property release of the intact protein.

An acid anhydride moiety reacts spontaneously with an —NH$_2$ group of a protein, e.g., a glycoprotein, under conditions of basic pH, e.g., as shown in FIG. 1, which results in reversible immobilization of the protein to a solid support, if the acid anhydride moiety is conjugated to the solid support. Even though many different functional groups exist in a protein or a protein sample such as, for example, —NH$_2$, —OH, COOH, and phenol groups, the reaction between acid anhydride with —NH$_2$ is selective. In some embodiments, however, an acid anhydride may also react with an —NHS group comprised in a protein, and immobilize the protein comprising the NHS group on a solid support conjugated to the acid anhydride moiety.

In some embodiments, a glycan, e.g., an N-glycan, is released from a glycoprotein under conditions of basic pH, e.g., 7-9. Most proteins are not denatured or fragmented under such mildly basic conditions, and the amide bond formed between the —NH$_2$ in the protein and the acid anhydride, e.g., the MAA, on the surface of the solid support is stable under such conditions as well. Thus, the methods provided herein allow for the reversible immobilization of a glycoprotein to a solid support via acid anhydride chemistry, and for deglycosylation, separation and/or isolation of the of released glycan portion, and subsequent release of the immobilized polypeptide portion of the glycoprotein.

In some embodiments, once the glycan fraction has been released and separated from an immobilized glycoprotein, the remaining polypeptide portion of the glycoprotein is released from the solid support. In some embodiments, this is achieved by lowering the pH, e.g., to pH 2-3, and, in some embodiments, by heating the solid support and the immobilized polypeptide portion in order to speed up the release reaction. The release reaction is an intra-molecular reaction resulting in a restoration of the acid anhydride moiety, e.g., of a five-member ring structure comprising an acid anhydride moiety in the case of using a maleic acid anhydride, a succinic acid anhydride, or a phthalic acid anhydride, or a derivative thereof, or any other five-membered ring acid anhydride. The generation of a five-membered ring acid anhydride at low pH is energy-favored. Thus, the release reaction requires much less energy compared to the hydrolysis of a standard linear amide bond ($-CO-NH_2$), e.g, within a protein back-bone. The cleavage of such linear amide bonds, e.g., within a protein backbone, typically requires harsh conditions, e.g., strong acidic condition (2M HCl and elevated temperature 60-70° C. for hours). In contrast, the cleavage of an amide bond formed by an acid anhydride can be achieved under much milder conditions, e.g., under mildly acidic conditions and/or at lower temperatures, thus allowing for a release of immobilized protein from acid anhydride-conjugated solid support while keeping the amide bonds in the immobilized protein intact. One particularly suitable acid anhydride for reversible immobilization of glycoproteins is maleic acid anhydride (MAA).

A wide variety of solid support materials can be used in the context of the methods and strategies for glycoprotein processing disclosed herein. In general, the solid support should be selected to be inert under the conditions and in the presence of the reagents encountered in the methods described herein, e.g., under conditions of basic and acidic pH and within the temperature range used to immobilize and release the polypeptide portion of a glycoprotein to the solid support as described herein. In some embodiments, the solid support takes the form of a bead, e.g., a polymer bead, a magnetic bead, a rigid bead, or a gel bead. In some embodiments, the diameter of the bead is in the range of 0.1 µm-1 mm, in the range of 1 µm-100 µm, in the range of 10 µm-100 µm, about 1 µm, about 10 µm, about 20 µm, about 30 µm, about 40 µm, about 50 µm, about 60 µm, about 70 µm, about 80 µm, about 90 µm, about 100 µm, about 200 µm, about 300 µm, about 400 µm, about 500 µm, about 600 µm, about 700 µm, about 800 µm, about 900 µm, or about 1 mm. In some embodiments, the solid support takes the form of a membrane, e.g., a membrane in a spin filter device. In some embodiments, the solid support takes the form of a surface of a culture or reaction vessel, e.g., of a test tube or a well in a multi-well plate.

In some embodiments, the solid support comprises a polymer, e.g., a polymer or copolymer described herein. Preferably, the polymer is inert under the reaction conditions described herein and allows for conjugation of acid anhydride moieties. In some embodiments, the solid support comprises a material, e.g. a polymer or copolymer, that is stable when heated up to at least 100° C. In some embodiments, the solid support comprises a material, e.g. a polymer or copolymer, that is stable over a broad range of pH conditions, e.g., from pH 1 to pH 14. In some embodiments, the solid support comprises polystyrene, polymethylmethacrylate, or silica. In embodiments, where the solid support comprises a carbohydrate-based polymer, such as, for example, cellulose or agarose, the solid support or the respective reaction conditions should be chosen so that the solid support does not interfere with the release of the glycan portion from the immobilized glycoprotein(s). For example, the choice of glycan-releasing enzyme should be such that the glycan portion from the glycoprotein(s) is released, but the solid support is not disintegrated. The surface of the solid support may be hydrophilic, but in some embodiments, a hydrophobic solid support surface may be preferred.

The methods and strategies described herein are useful for the release and capture of the glycan portion of a glycoprotein and can also be used to subsequently capture the polypeptide portion of the same glycoprotein. Accordingly, the methods and strategies described herein can be used to analyze the glycosylation of a protein or a population of proteins. However, as will be understood by those of skill in the art, the disclosure is not limited to the release and capture of glycans from glycoproteins, but can be applied to the release and/or capture of other post-translational modification (PTM) of proteins as well, such as, for example, glycation, myristoylation, almitoylation, isoprenylation or prenylation, farnesylation, geranylgeranylation, glypiation, glycosylphosphatidylinositol (GPI) anchor formation via an amide bond to C-terminal tail, lipoylation, flavin moiety (FMN or FAD) attachment, heme C attachment, phosphopantetheinylation, retinylidene Schiff base formation, diphthamide formation, ethanolamine phosphoglycerol attachment, hypusine formation, acylation, e.g. O-acylation (esters), N-acylation (amides), S-acylation (thioesters), acetylation, formylation, alkylation, methylation, amidation, arginylation, polyglutamylation, polyglycylation, butyrylation, gamma-carboxylation, polysialylation, malonylation, hydroxylation, iodination, ribosylation, phosphate ester (O-linked) or phosphoramidate (N-linked) formation, phosphorylation, adenylylation, propionylation, pyroglutamate formation, S-glutathionylation, S-nitrosylation, succinylation, sulfation, selenoylation, biotinylation, pegylation, ISGylation, SUMOylation, ubiquitination, Neddylation, Pupylation, citrullination, deamidation, eliminylation, or carbamylation. In general, the methods provided herein allow for a release and capture of the PTM moiety, and also for a subsequent capture of the respective polypeptide portion of the protein comprising the PTM. It will be apparent to the skilled artisan, that the surface chemistry of the solid support as well as the buffers and reagents used for release of the respective PTM will depend on the nature of the PTM to be released and captured.

Optional Pre-Processing: Alkylation and Reduction of Glycoproteins

In some embodiments, a method provided herein comprises a reduction and/or alkylation step. Such steps are particularly useful if separation and/or isolation of glycans and polypeptides from glycoproteins comprising cysteine residues is attempted. Cysteine residues can form disulfide (S—S)-bonds, which stabilize the 3-D structure of proteins, and may hinder the release of glycans from the glycoprotein. The release of glycans may be facilitated in some embodiments by reducing disulfide bonds and/or by alkylating any present thiol groups. For example, in some embodiments comprising an enzymatic release of a glycan from a cysteine residue-comprising glycoprotein is attempted, the method comprises a step of contacting the glycoprotein with a reduction agent and/or an alkylating agent. In some embodiments, the reduction agent is provided in an amount sufficient to dissociate a cysteine bridge (S—S disulfide bonds) in the glycoprotein. In some embodiments, the reduction agent is provided in an amount sufficient to dissociate all cysteine bridges (S—S disulfide bonds) in the glycoprotein. In some embodiments, the glycoprotein is contacted with an alkylating agent. In some embodiments, the alkylating agent is provided in an amount sufficient to alkylate the S-moiety of a reduced cysteine residue in the glycoprotein. In some embodiments, the alkylating agent is provided in an amount sufficient to alkylate all reduced S-moieties of reduced cysteine residues comprised in the glycoprotein.

Reduction and/or alkylation are useful to achieve efficient enzymatic release of glycans from glycoproteins by reducing steric hindrance of enzyme access to glycans through reduction of secondary and higher structures of glycoproteins, resulting in an "open" or linearized amino acid sequence, and thus facilitating enzyme access, e.g., PNGase F access to target glycan groups. Reduction and/or alkylation can also be used to attach a specific alkyl group to those cysteine residues that form S—S bonds in the native glycoprotein. Such specific alkyl groups can serve as readily identifiable tags in subsequent analytic approaches, such as mass spectroscopy assays.

Methods and reagents for reduction and alkylation of proteins, including glycoproteins, are well known to those in the art. Some exemplary methods and reagents (e.g., DTT/IAA) are described in more detail elsewhere herein. Additional suitable methods and reagents will be apparent to those of skill in the art based on the instant disclosure. The disclosure is not limited in this respect.

In some embodiments, a method involving release of a glycan from a glycoprotein, as provided herein, comprises a step of purifying the reduced and/or alkylated glycoprotein after reduction and/or alkylation. In some embodiments, reduction and/or alkylation are effected prior to immobilization of the glycoprotein to the solid support. In some such embodiments, the purification comprises a buffer exchange in a filter column. Suitable reducing and alkylating reagents for such embodiments typically have a lower molecular weight than the reduced and/or alkylated glycoproteins produced as a result of the reduction and/or alkylation. In other embodiments, the reduction and/or alkylation is performed after the glycoprotein has been immobilized on a solid support. In some such embodiments, a purification step may comprise washing away any unused alkylation or reduction agent by washing the solid support with an appropriate wash buffer. The solid support in such embodiments should be chosen to not interfere with the reduction and/or alkylation, e.g., the solid support should consist of material (s) that are inert to the reduction and/or alkylating agents used.

Downstream Applications

The technology provided herein can be used to isolate glycans and/or polypeptides for any suitable downstream application, for example, for further analysis, identification, measuring, and/or quantification of the isolated glycans and/or polypeptides. Because the technology provided herein allows for the separation and isolation of both a glycan and a polypeptide portion from a glycoprotein, it is particularly suitable for downstream applications that benefit from the availability of both portions. However, it will be understood that the instantly provided technology is not limited to such downstream applications.

In some embodiments, the technology provided herein is applied in the context of a diagnostic method. For example, a glycan and/or polypeptide portion of a glycoprotein may be obtained from a subject using the instantly disclosed technology, and may subsequently be analyzed. In some embodiments a glycan and/or polypeptide portion of a glycoprotein is obtained from a sample from the subject, for example, a tissue, or a body fluid sample.

The term body fluid, as used herein, refers to any body fluid including, without limitation, serum, plasma, lymph fluid, synovial fluid, follicular fluid, seminal fluid, amniotic fluid, milk, whole blood, sweat, urine, cerebrospinal fluid, saliva, semen, sputum, tears, perspiration, mucus, ascites fluid, interstitial fluid, tissue culture medium, tissue extracts, and cellular extracts. It may also apply to portions and dilutions of body fluids. The source of a body fluid can be a human body, an animal body, an experimental animal, a plant, or other organism.

The technology provided herein can be applied in the context of samples obtained from a subject. The subject, in some embodiments, is a human. In some embodiments, the subject is a mammal, a mouse, a rat, a cat, a dog, a cattle, a goat, a pig, a sheep, a vertebrate, a fish, a reptile, an amphibian, an insect, a fly, an annelid, or a nematode. The technology described herein is, however, not limited to such samples, and can be applied to samples from other sources as well, for example, to samples obtained from bacteria, yeast, plants, or from environmental samples.

In some embodiments, a glycan and/or a polypeptide portion isolated from a glycoprotein via the instantly disclosed technology is analyzed for the presence or absence of a biomarker. In some embodiments, the biomarker is indicative of the presence or absence of a parameter of interest, for example, a biomarker associated with a disease or disorder is indicative of the absence or the presence of disorder in the subject the sample was derived from. For another example, the presence of a biomarker, for example, a specific glycan structure, may be indicative of the presence of an organism, e.g., a pathogenic organism, in a sample.

Glycan and polypeptide biomarkers useful according to aspects to this disclosure will be apparent to those of skill in the art. The skilled artisan will, for example, be aware of glycan and/or polypeptide biomarkers associated with a disease or disorder in a human subject.

Another exemplary, non-limiting downstream application for which the technology disclosed herein is suited is the quality control of proper glycosylation of engineered proteins. Engineered proteins frequently require proper glycosylation to exert their function. For example, antibodies, and antibody fragments are most effective if properly glycosylated, and aberrant or lacking glycosylation abrogates proper function. Accordingly, the technology described herein can be used to monitor glycosylation in engineered proteins, for example, in proteins produced for therapeutic purposes, or for biotechnological applications, such as substrate fermentation.

The term antibody, as used herein, refers to an immunoglobulin molecule or an immunologically active portion thereof (e.g., antigen-binding portion). The antibody may be naturally produced or wholly or partially synthetically produced. Examples of immunologically active portion of immunoglobulin molecules include F(ab), Fv, and F(ab') fragments which can be generated by cleaving the antibody with an enzyme such as pepsin. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are generally preferred in the context of the present disclosure.

The term antibody fragment refers to any derivative of an antibody which is less than full-length. Preferably, the antibody fragment retains at least a significant portion of the full-length antibody's specific binding ability. Examples of antibody fragments include, but are not limited to, Fab, Fab', $F(ab')_2$, scFv, Fv, dsFv diabody, and Fd fragments. The antibody fragment may be produced by any means. For instance, the antibody fragment may be enzymatically or chemically produced by fragmentation of an intact antibody, or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages or other more stable linkages. The fragment may also optionally be a multimolecular complex. A functional antibody fragment will typically comprise at least about 50 amino acids and more typically will comprise at least about 200 amino acids. In certain embodiments, the antibody fragment has at least two antigen-binding site. In certain preferred embodiments, the antibody fragment has exactly 2, 3, 4, or 5 antigen-binding sites. Fragments with two antigen-binding sites are particularly useful according to aspects of the present disclosure.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. Diabodies are dimeric scFvs. The components of diabodies typically have shorter peptide linkers than most scFvs, and they show a preference for associating as dimers. An Fv fragment is an antibody fragment which consists of one $V_H$ and one $V_L$ domain held together by noncovalent interactions. The term dsFv is used herein to refer to an Fv with an engineered intermolecular disulfide bond to stabilize the $V_H$-$V_L$ pair. A $F(ab')_2$ fragment is an antibody fragment essentially equivalent to that obtained from immunoglobulins (typically IgG) by digestion with an enzyme pepsin at pH 4.0-4.5. The fragment may be recombinantly produced. A Fab fragment is an antibody fragment essentially equivalent to that obtained by reduction of the disulfide bridge or bridges joining the two heavy chain pieces in the $F(ab')_2$ fragment. The Fab' fragment may be recombinantly produced. A Fab fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

The skilled artisan will be aware of numerous engineered proteins that require proper glycosylation for proper function. Such proteins include, for example, any therapeutic proteins approved for therapeutic use in human subject.

Additional downstream applications suitable for further processing and/or analysis of a glycan and/or a polypeptide obtained via the instantly disclosed technology will be apparent to those of skill in the art. The disclosure is not limited in this respect.

Devices

Some aspects of this disclosure provide a device for separating and/or isolating a glycan portion and/or a polypeptide portion from a glycoprotein. In some embodiments, the device comprises a solid support comprising a reactive moiety that binds the polypeptide portion of the glycoprotein. In some embodiments, the reactive moiety is an anhydride moiety, e.g., a maleic acid anhydride moiety, a succinic acid moiety, or a phthalic acid anhydride moiety. In some embodiments, the solid support is in the form of a bead or resin. In some embodiments, the device comprises a compartment comprising the solid support. In some embodiments, the device comprises a compartment that can hold a sample comprising a glycoprotein. In some embodiments, the compartment comprising the solid support and the compartment comprising the sample are the same compartment. In some embodiments, the device is a column comprising the solid support and allowing for a sample comprising a glycoprotein to flow through the column while contacting the solid support. In some embodiments, the column is a liquid chromatography column. In some embodiments, the column is a spin column. In some embodiments, a spin column comprises an outer centrifugation vessel, for example, a 1.5 ml, 10 ml, or 50 ml centrifuge tube that serves as a collection compartment, and a cartridge that can be inserted into the centrifuge tube, which holds the solid support. The cartridge typically comprises a fluid reservoir, into which a fluid sample, e.g., a sample comprising a glycoprotein, or a wash or elution buffer, can be transferred, and a liquid-permeable surface, e.g., a frit or membrane through which the liquid sample, but not the solid support can pass. A range of columns that can be loaded with custom solid support, e.g., with custom resin or beads and suitable for processing different volumes of fluid samples are commercially available. In some embodiments, a membrane is used as the solid support. In some embodiments, the membrane is hydrophobic. In some embodiments, the membrane is hydrophilic.

The methodology provided herein can be performed on a small, laboratory scale, or on a large, industrial scale. The devices provided herein can be scaled in size to allow for the processing of the required sample size. For example, in some embodiments, a device is provided that is suitable for processing a sample comprising a glycoprotein of a sample volume of about 1 µl, about 2 µl, about 5 µl, about 10 µl, about 50 µl, about 100 µl, about 250 µl, about 500 µl, about 1 ml, about 2 ml, about 5 ml, about 10 ml, about 15 ml, about 50 ml, about 100 ml, about 250 ml, about 500 ml, about 1 L, about 2 L, about 5 L, about 10 L, about 50 L, about 100 L, about 250 L, or about 500 L. In some embodiments, a device provided herein is suitable for the processing of a single sample, e.g., a device that comprises a single sample compartment, and a single collection compartment. In other embodiments, a device is provided herein that allows for the simultaneous processing of a plurality of samples. In some embodiments, such a multi-sample device comprises a multi-well plate. In some such embodiments, the device comprises a first plate with multiple wells, in which each well functions as a sample compartment, a weight/size-selective material, e.g., a semi-permeable membrane, at the bottom of each well, and a second plate comprising the same number of wells, which function as the collection compartment. The first plate can be assembled to fit into the second plate, and the plate assembly can then be placed into a centrifuge for sample filtration.

In some embodiments, the collection compartment is detachable from the sample compartment. In some embodiments, the collection compartment is replaceable. For example, in some embodiments, a first collection compartment is used in pre-processing of the sample, e.g., to reduce or alkylate a glycoprotein, or to immobilize a glycoprotein on the solid support. In some embodiments, prior to the release and/or separation of a glycan portion from the glycoprotein, the first collection compartment is replaced by a second collection compartment, which is used to collect the glycan portion. In some embodiments, a detachable collection compartment is a disposable, single-use tube. In some embodiments, the collection compartment is shaped to fit a centrifuge. In some embodiments, the collection compartment fits a vacuum centrifuge. This is of particular benefit if the separated glycan or and/or polypeptide portions are to be dried after separation. In some embodiments, the collection compartment can be used for storage and/or further processing, without the need for transferring the eluted portion to another vessel. In some embodiments, the collection compartment comprises a lid.

In some embodiments, the device is made to withstand the forces, temperatures, conditions, and materials it is exposed to during sample processing. For example, the device, in some embodiments, is made to withstand centrifugal forces of at least 10,000 g, a pH range from 1-13, and temperatures from 4° C. to 100° C. In some embodiments, the device is made to withstand microwave irradiation to the extent used in the technology described herein.

Kits

Some aspects of this disclosure provide a kit for separating a glycan and/or a polypeptide from a glycoprotein. In some embodiments, the kit comprises a solid support for immobilizing a glycoprotein as described herein. In some embodiments, the kit comprises a device for separating a glycan and/or a polypeptide portion of a glycoprotein as described herein. In some embodiments, the kit also comprises a buffer or reagent suitable for immobilizing a glycoprotein on a solid support as described herein, and/or for separating a glycan and a polypeptide portion of a glycoprotein. In some embodiments, the kit comprises a glycosidase. In some embodiments, the glycosidase comprises an endoglycosidase. In some embodiments, the kit comprises an exoglycosidase. In some embodiments, the glycosidase comprises one or more endoglycosidases selected from the group comprising peptide N-glycosidase F, endoglycosidase H, endoglycosidase Hf, peptide N-glycosidase A, and O-glycanase. In some embodiments, the kit comprises $O^{18}$ water. In some embodiments, the endoglycosidase is in a solution comprising $O^{18}$ water. In some embodiments, the kit comprises a basic pH buffer. In some embodiments, the kit comprises an acid pH buffer. In some embodiments, the acid pH buffer comprises formic acid, trifluoro-acetic acid, or acetic acid. In some embodiments, the kit comprises a protease. In some embodiments, the protease is trypsin. In some embodiments, the kit comprises instructions for separating a glycan and a polypeptide.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Methods for reversible immobilization of a glycoprotein to a solid support via acid anhydride chemistry was developed that allows for the release of a glycan portion from the immobilized glycoprotein, and for subsequent separation of the released glycan portion from the immobilized polypeptide portion of the glycoprotein. Solid-phase maleic acid anhydride (SPMAA) was used to immobilize glycoproteins. FIGS. 1-4 illustrate the MAA surface chemistry before contacting with the glycoprotein, the reversible immobilization of a glycoprotein to the SPMAA by covalent conjugation via anhydride chemistry, washing and/or purifying the immobilized glycoprotein, release and capture of a glycan from the immobilized glycoprotein, and release and capture of the polypeptide portion of the glycoprotein.

A model glycoprotein, RNase B, was immobilized on SPMAA. The SPMAA used was maleic acid anhydride grafted onto a modified cellulose polymer. First, the SPMAA was subjected to an acidic pre-wash step with 50 mM HCl solution. Other acids, such as $H_2SO_4$ can also be used. The pre-wash was performed to remove any residual materials that may remain on the SPMAA after synthesis and storage. The pre-wash would also remove any storage solution, including non-aqueous storage solution.

After pre-washing, the SPMAA was contacted with RNase B under conditions of physiologic to basic pH (pH 7-9). A sample comprising the RNase B was contacted to the SPMAA to immobilize RNase B on the SPMAA. While not necessary for protein immobilization, insoluble proteins in the sample may be brought into solution by the addition of a detergent. The detergent should be selected to not include any primary $NH_2$ groups, as they may interfere with MAA chemistry-based protein immobilization.

Once the proteins are immobilized, active MAA functional moieties that did not bind a protein on the SPMAA surface were blocked in order to avoid interference of these MAA moieties with subsequent processing. For example, such active MAA moieties may bind and immobilize a glycosidase enzyme used for releasing the glycan protein from the immobilized glycoproteins. The blocking was achieved by contacting the SPMAA with a small molecule comprising a primary —$NH_2$ group, for example, ethylamine ($CH_3CH_2NH_2$), which can react to the unbound MAA quickly. Other molecules comprising a primary $NH_2$ group can also be used.

Glycans were released from the immobilized RNase B via contacting the immobilized RNase B with PNGase F. For this, the SPMAA was washed with the buffer used for enzymatic release of glycans from the immobilized glycoproteins. Here, PBS (pH 7.4) was used. Other buffers, e.g. buffers that support enzymatic release of glycans from glycoproteins, can also be employed. Reduction and alkylation of proteins can be incorporated at this stage, or can be performed prior to protein immobilization on the SPMAA.

PNGase F digestion of the SPMAA-immobilized proteins was performed overnight. The released glycans were extracted from the SPMAA by elution with water, leaving the deglycosylated polypeptide portion of RNase B (DG-R) immobilized on the SPMAA.

The immobilized, deglycosylated polypeptide portion of RNase B was then released from the SPMAA by lowering the pH to pH 2-3 and captured. Release of the de-glycosylated RNase B proteins from the SPMAA was achieved by contacting the SPMAA with 5% formic acid solution and incubation for 12 hours. The released RNase B was recovered in the formic acid solution.

Figure 5:
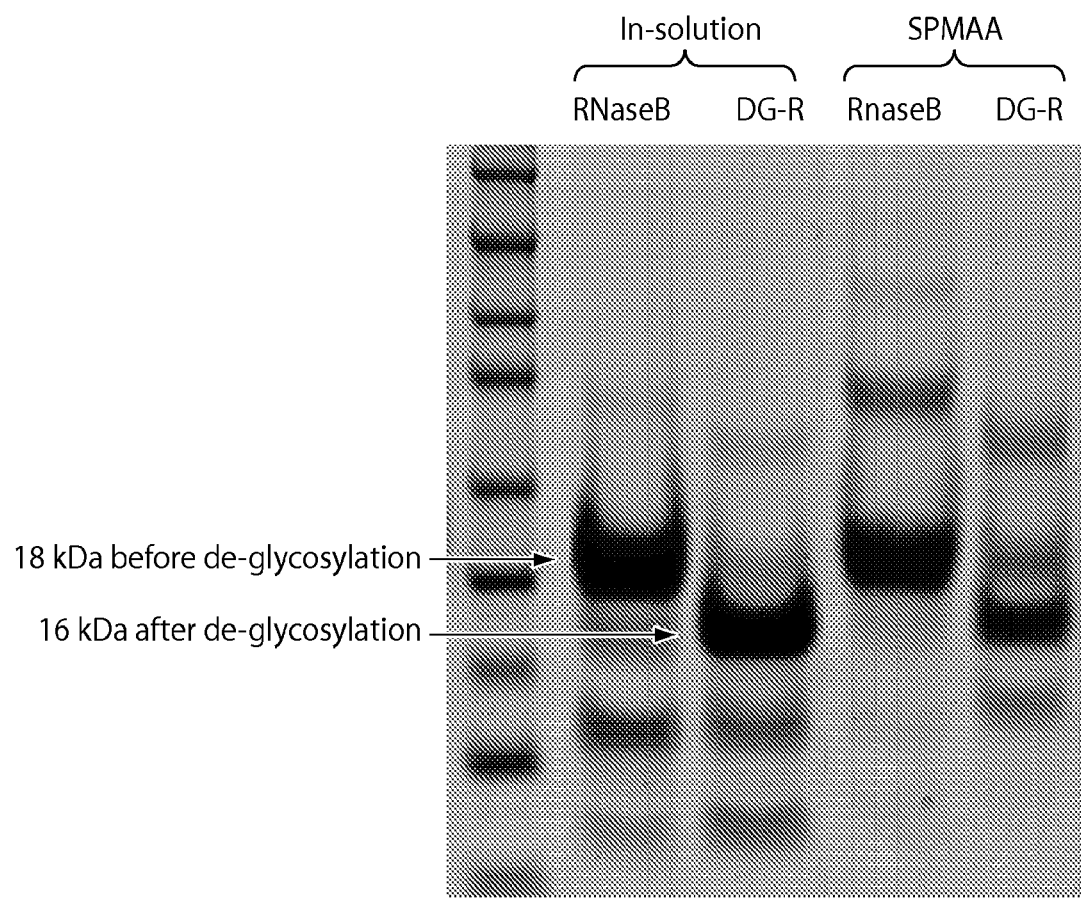
FIG. 5 shows gel bands representing a glycoprotein before and after immobilization, de-glycosylation, release and recapture. A model glycoprotein, RNase B, was immobilized on solid-phase maleic acid anhydride (SPMAA). Glycans were released from the immobilized RNase B and captured, leaving the deglycosylated polypeptide portion of RNase B (DG-R) immobilized on the SPMAA. Finally, the immobilized, deglycosylated polypeptide portion of RNase B was released from the SPMAA and captured.

The glycosylated RNase B immobilized onto the SPMAA as well as the captured de-glycosylated RNase B recovered from the SPMAA was run on a gel and compared to controls of RNase in glycosylated and de-glycosylated form, generated by conventional liquid-phase methods (FIG. 5).

Figures 1, 6:
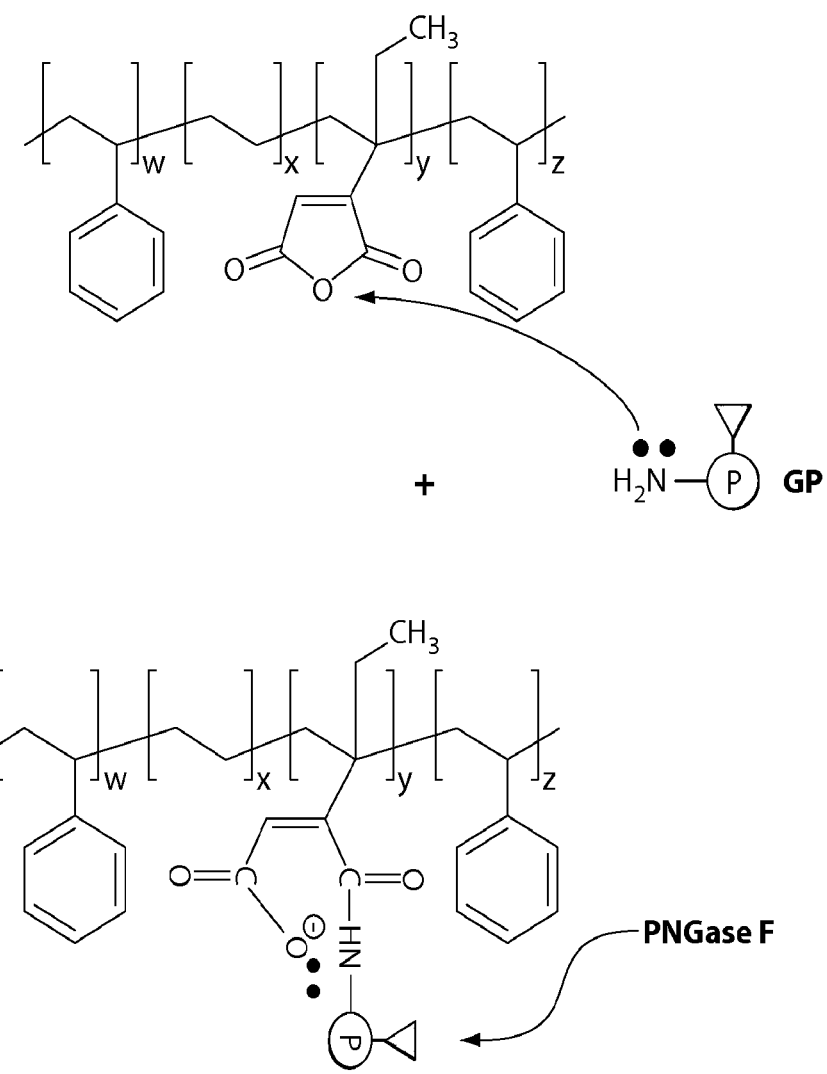
FIG. 6 illustrates an exemplary embodiment of immobilization of RNase B to a solid support comprising polystyrene-grafted MAA, washing and/or purifying the immobilized RNase B, and release and capture of the glycan portion from the immobilized RNase B. The captured glycan portion was subjected to mass spectrometry (MS) analysis to identify the identity of the captured glycan molecules and to determine the glycan profile of RNase B. The MS spectrum and the structure of some glycans detected is shown in the lower panel.
Figures 2, 6:
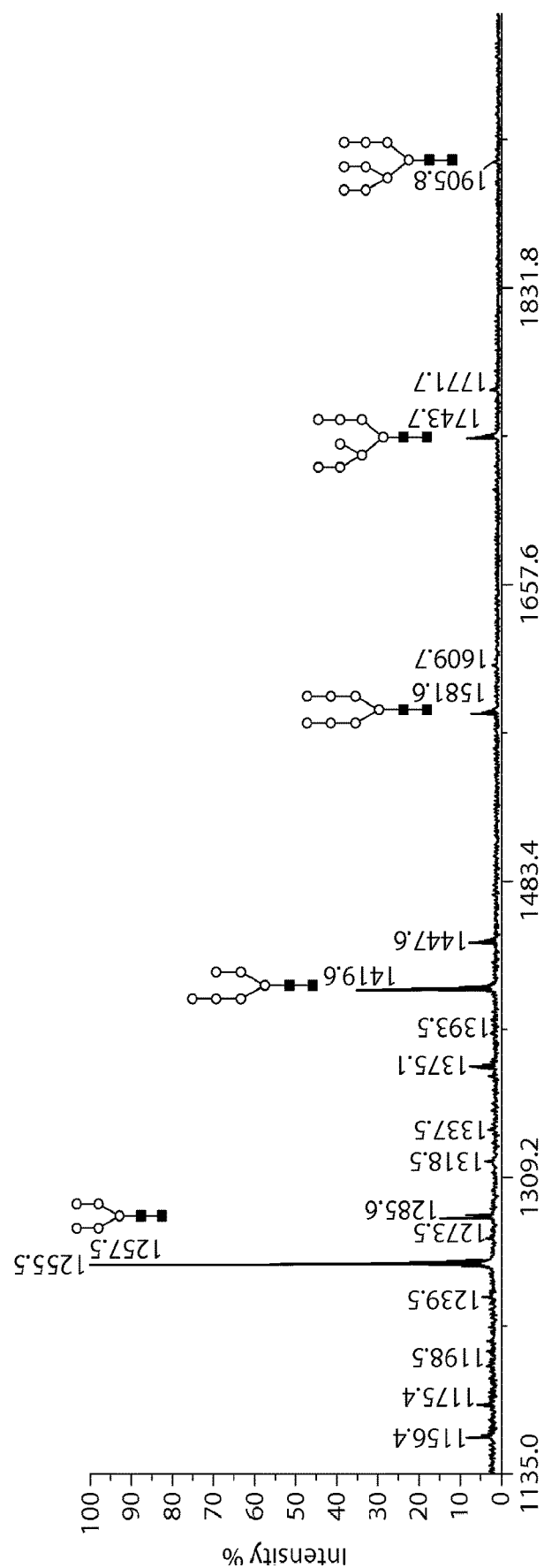

For analysis of the glycan profile of RNase B, glycans released from SPMAA-immobilized RNase B were captured and analyzed by mass spectrometry (FIG. 6). The SPMAA used was polystyrene-block-poly(ethylene-ran-butylene)-block-polystyrene-graft-maleic anhydride (Sigma-Aldrich, St Louis, Mo., USA, Cat #432431, CAS Number 124578-11-6, MDL number MFCD00241501, PubChem Substance ID 24867088). The SPMAA used was in the form of beads. The pre-washing, immobilization, and glycan-release steps were as described above. The captured glycan portion released from RNase B was subjected to mass spectrometry, to identify the structure of the captured glycan molecules and to determine the glycan profile of RNase B (FIG. 6). The MS spectrum and the structure of some of the glycans detected is shown in the lower panel.

Figure 7:
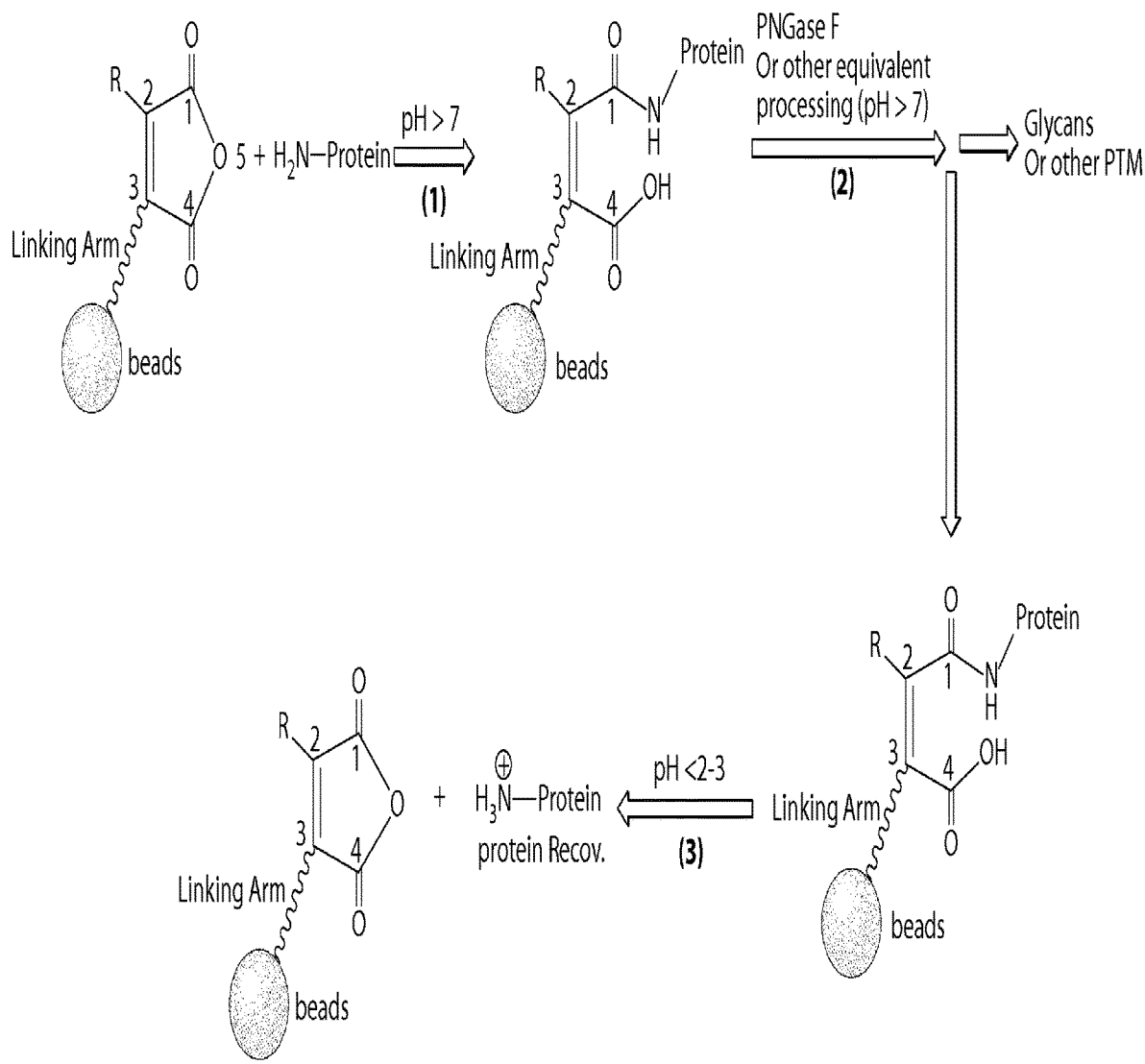
FIG. 7 illustrates an exemplary embodiment of immobilization of a glycoprotein to a bead comprising MAA on its surface, washing and/or purifying the immobilized glycoprotein, release and capture of the glycan portion or other post-translational modification (PTM) from the immobilized glycoprotein, and release and capture of the polypeptide portion of the glycoprotein.

FIG. 7 shows a general schematic of one of the methods developed for reversible immobilization of glycoproteins that allows release and capture of the glycan portion and subsequent release and capture of the polypeptide portion using a maleic acid anhydride chemistry on the surface of beads. SPMAA is contacted with a glycoprotein at basic pH, e.g., at pH 7-9, resulting in covalent immobilization of the glycoprotein on the surface of the beads. The SPMAA is then washed with washing buffer at pH 7, removing any unbound components from the beads. PNGase F treatment is effected at pH 7, releasing the glycan portion of the immobilized glycoproteins. The glycan fraction is captured by elution and can subsequently be subjected to downstream analysis, e.g., mass spectrometry. After washing at pH 7 with wash buffer, the SPMAA is contacted with a solution at pH<2-3, resulting in a release of the immobilized polypeptide portion of the glycoprotein from the SPMAA. The released glycoprotein portion is then captured by elution, and can be subjected to downstream analysis, e.g., mass spectrometry.

REFERENCES

All publications, patents, patent applications, publication, and database entries (e.g., sequence database entries) mentioned herein, e.g., in the Background, Summary, Detailed Description, or Examples sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method of separating a glycan from a glycoprotein comprising the glycan bound to a polypeptide portion of the glycoprotein, the method comprising:

(a) contacting the glycoprotein with a solid support comprising an acid anhydride (AA) moiety directly conjugated on its surface, wherein the AA moiety reacts with an —NH2 or —NHS group in the polypeptide and forms a covalent bond between the solid support and the polypeptide;

(b) cleaving a bond between the glycan and the polypeptide; and (c) separating the glycan from the polypeptide;

wherein the AA moiety is selected from the group consisting of:

(i) formula MAA-1:

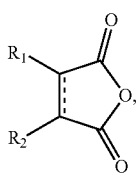

(Formula MAA-1)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —N($R_B$)$_2$; —NHC(O)$R_B$; or —C($R_B$)$_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio;

(ii) Formula MAA-2:

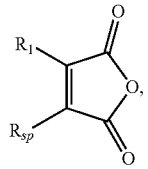

(Formula MAA-2)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_{sp}$ represents a solid support or a molecule or moiety that binds or conjugates to a solid support;

(iii) formula PAA-1:

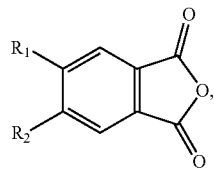

(Formula PAA-1)

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$;

—CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and (iv) Formula PAA-2:

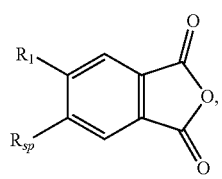

(Formula PAA-2)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_{sp}$ represents a solid support or a molecule or moiety that binds or is conjugated to a solid support.

2. The method of claim 1, wherein the acid anhydride moiety is a maleic acid anhydride (MAA) moiety of formula MAA-1:

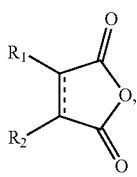

(Formula MAA-1)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

3. The method of claim 1, wherein the acid anhydride moiety is a maleic acid anhydride (MAA) moiety of Formula MAA-2:

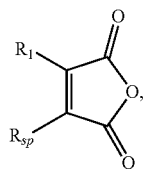

(Formula MAA-2)

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and R$_{sp}$ represents a solid support or a molecule or moiety that binds or conjugates to a solid support (e.g., via a linker).

4. The method of claim 1, wherein R1 and/or R2 are, independently, hydrogen, methyl (—CH$_3$), trichloromethyl (—CCl$_3$), or trifluoromethyl (—CF$_3$).

5. The method of claim 1, wherein the glycoprotein is contacted with the solid support at basic pH.

6. The method of claim 1, wherein cleaving the bond between the glycan and the polypeptide comprises contacting the glycoprotein with an endoglycosidase.

7. The method of claim 6, wherein the endoglycosidase comprises a peptide N-glycosidase F.

8. The method of claim 6, wherein cleaving the bond between the glycan and the polypeptide further comprises contacting the glycoprotein with O$^{18}$ water.

9. The method of claim 1, wherein cleaving the bond between the glycan and the polypeptide further comprises exposing the glycoprotein to microwaves.

10. The method of claim 9, wherein the microwaves are generated by a domestic microwave.

11. The method of claim 1, wherein the glycan is separated from the polypeptide bound to the solid support via elution.

12. The method of claim 11, wherein the elution is at basic or neutral pH.

13. The method of claim 1, wherein the method further comprises releasing the bound polypeptide from the solid support.

14. The method of claim 1, wherein the acid anhydride moiety is a phthalic acid anhydride (PAA) moiety of formula PAA-1:

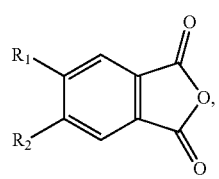

(Formula PAA-1)

wherein
- $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and
- $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —N($R_B$)$_2$; —NHC(O)$R_B$; or —C($R_B$)$_3$; wherein each occurrence of $R_B$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio.

15. The method of claim 1, wherein the acid anhydride moiety is a phthalic acid anhydride (PAA) moiety of formula PAA-2:

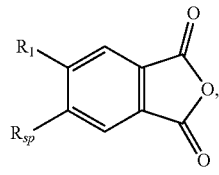

(Formula PAA-2)

wherein
- $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched alkyl; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently hydrogen, a protecting group, aliphatic, heteroaliphatic, alkyl, acyl, aryl, heteroaryl, alkoxy, aryloxy, alkylthio, arylthio, amino, alkylamino, dialkylamino, heteroaryloxy, or heteroarylthio; and
- $R_{sp}$ represents a solid support or a molecule or moiety that binds or is conjugated to a solid support.

* * * * *